(12) United States Patent
Yamamoto et al.

(10) Patent No.: US 10,060,850 B2
(45) Date of Patent: Aug. 28, 2018

(54) PARTICLE DETECTION USING REFLECTIVE SURFACE

(71) Applicant: CAPTL LLC, West Lafayette, IN (US)

(72) Inventors: Masanobu Yamamoto, West Lafayette, IN (US); J. Paul Robinson, West Lafayette, IN (US)

(73) Assignee: CAPTL LLC, West Lafayette, IN (US)

( * ) Notice: Subject to any disclaimer, the term of this patent is extended or adjusted under 35 U.S.C. 154(b) by 0 days.

(21) Appl. No.: 15/564,117

(22) PCT Filed: Apr. 1, 2016

(86) PCT No.: PCT/US2016/025650
§ 371 (c)(1),
(2) Date: Oct. 3, 2017

(87) PCT Pub. No.: WO2016/161337
PCT Pub. Date: Oct. 6, 2016

(65) Prior Publication Data
US 2018/0080870 A1 Mar. 22, 2018

Related U.S. Application Data

(60) Provisional application No. 62/142,818, filed on Apr. 3, 2015, provisional application No. 62/211,452, filed on Aug. 28, 2015.

(51) Int. Cl.
*G01N 21/47* (2006.01)
*G01N 15/14* (2006.01)

(52) U.S. Cl.
CPC ......... *G01N 21/47* (2013.01); *G01N 15/1434* (2013.01)

(58) Field of Classification Search
CPC ...... G01N 21/47; G01N 21/55; G01N 21/645; G01N 15/1434; G01N 15/1425;
(Continued)

(56) References Cited

U.S. PATENT DOCUMENTS 5,946,287 A 8/1999 Nakayama et al.
6,181,657 B1 1/2001 Kuroda et al.
(Continued)

FOREIGN PATENT DOCUMENTS

WO WO2014/206584 12/2014
WO WO2016/161337 10/2016

OTHER PUBLICATIONS

Chen, et al., "The Photon Counting Histogram in Fluorescence Fluctuation Spectroscopy", Biophysical Journal, vol. 77, Jul. 1999, pp. 553-567.
(Continued)

*Primary Examiner* — Sang Nguyen
(74) *Attorney, Agent, or Firm* — Lee & Hayes, PLLC; Christopher J. White

(57) ABSTRACT

An example assembly includes a target holder that retains a target in a detection region. A reflective surface reflects at least part of a focused spot of light to provide resultant light. An irradiation system irradiates at least part of the detection region with the focused spot of light. A motion system causes motion of the focused spot of light relative to the reflective surface. A detection system detects the resultant light. An example device, e.g., a lab-on-chip, includes a substrate, a sample inlet, and a reflective grating. The grating is retains a fluidic sample in a detection region fluidically connected to the sample inlet. The detection region is operatively arranged with respect to the reflective grating so that at least a portion of light passing through the detection region towards the reflective grating also passes through the detection region after reflecting off the reflective grating.

18 Claims, 24 Drawing Sheets

(58) Field of Classification Search
CPC .............. G01N 15/147; G01N 15/1484; B01L 3/502715; B01L 2300/0654; B01L 2300/0806; B01L 2300/168; C12M 1/42; C12M 1/34; C12Q 1/24

See application file for complete search history.

(56) References Cited

U.S. PATENT DOCUMENTS

| | | | |
|---|---|---|---|
| 6,280,960 | B1 | 8/2001 | Carr |
| 6,377,341 | B1* | 4/2002 | Rowlen ................. G01N 21/41 356/128 |
| 6,532,208 | B2 | 3/2003 | Nakajima |
| 7,280,204 | B2 | 10/2007 | Robinson et al. |
| 8,634,076 | B2 | 1/2014 | McNeil-Watson |
| 9,222,834 | B2* | 12/2015 | Den Boef ............. G01J 3/4412 |
| 2001/0000696 | A1 | 5/2001 | Kuroda et al. |
| 2002/0085202 | A1 | 7/2002 | Gordon |
| 2006/0085202 | A1* | 4/2006 | Sahlberg ............. G06F 3/03545 709/229 |
| 2006/0166216 | A1 | 7/2006 | Nakao et al. |
| 2007/0003436 | A1* | 1/2007 | Nolte ................. G01B 11/2441 422/64 |
| 2007/0109542 | A1* | 5/2007 | Tracy ................... G01N 21/553 356/445 |
| 2011/0267623 | A1* | 11/2011 | Matejka ............... G01N 21/278 356/446 |
| 2013/0316394 | A1 | 11/2013 | Stimpson |
| 2013/0316396 | A1* | 11/2013 | Fricking ................ C12M 27/16 435/41 |
| 2014/0072997 | A1* | 3/2014 | Yamamoto ............. G01N 15/14 435/30 |
| 2014/0339446 | A1* | 11/2014 | Yamamoto ......... G01N 15/1434 250/576 |
| 2014/0364588 | A1 | 12/2014 | Haugwitz et al. |
| 2015/0204664 | A1* | 7/2015 | Bringoltz ............ G03F 7/70683 356/492 |
| 2017/0059485 | A1 | 3/2017 | Yamamoto |

OTHER PUBLICATIONS

Cmditrwiki, "Two-Photon Spectroscopy", Jun. 16, 2011, retrieved Aug. 23, 2016 from <<http://photonicswiki.org/index.php?title=Two-Photon_Spectroscopy>>, 2 pages.

"Exosomes & Microvesicles Application Note", Nanosight, Mar. 2014. Retrieved Mar. 30, 2015 at <<http://www.nanosight.com/applications/exosomes-amp-microvesicles-application-notes>>, 5 pages.

Givan, "Flow Cytometry: First Principles, Second Edition", 2001, Wiley-Liss, Inc. pp. 15-80.

Hamamatsu, "Photon Counting: Using Photomultiplier Tubes", Apr. 2001, 31 pages.

Konokhova, A.I., "Light-Scattering Flow Cytometry for Identification and Characterization of Blood Microparticles", Journal of Biomedical Optics, vol. 17, No. 5, May 2012, 9 pages.

"Mastering of Blu-ray Disc", Singulus Mastering, May 14, 2007, 21 pages.

Michalet, et al., "New Photon-Counting Detectors for Single-Molecule Fluorescence Spectroscopy and Imaging", Proc. of SPIE, vol. 8033, 2011, 12 pages.

"Nanoparticle Tracking Analysis", Malvem, Aug. 18, 2014, retrieved Mar. 18, 2016 from <<http://www.malvem.com/en/products/technology/nanoparticle-tracking-analysis/default.aspx>>, 3 pages.

Nix, Roger, "5.3 Photoelectron Spectroscopy" Jul. 2014, retrieved Aug. 23, 2016, <<http://www.chem.qmul.ac.uk/surfaces/scc/scat5_3.htm>>, 8 pages.

PCT Search Report and Written Opinion dated Aug. 17, 2016 for PCT Application No. PCT/US16/25650, 14 pages.

"Photoelectron Spectroscopy", University of Liverpool, Feb. 2016, 2 pages.

"Richardson Gratings—Technical Note 3", Oct. 30, 2013, retrieved Aug. 22, 2016, from <<http://www.gratinglab.com/information/Technical_NotesfTechNote3.aspx>>, 3 pages.

Schwille, et al., "Fluorescence Correlation Spectroscopy" Max-Planck-Institute for Biophysical Chemistry, May 17, 2004, retrieved from <<https://www.biophysics.org/Portals/1/PDFs/Education/schwille.pdf>>, 33 pages.

Tian, et al., "Blu-ray Optomagnetic Measurement Based Competitive Immunoassay for *Salmonella* Detection", BioSensors and Bioelectronics 77, 2016, pp. 32-39.

Tian, et al., "Blue-ray Optomagnetic Measurement Based Competitive Immunoassay for *Salmonella* Detection—Supplementary Material", BioSensors and Bioelectronics 77, 2016, 11 pages.

Totoki, et al., "Quantitative Laser Diffraction Method for the Assessment of Protein Subvisible Particles", Journal of Pharmaceutical Sciences, 2015, vol. 104, pp. 618-626.

Van der Pol, Edwin, "Detection of Microparticles by Flow Cytometry", Biomedical Engineering and Physics Laboratory Experimental Clinical Chemistry, May 21, 2013, 28 pages.

Van der Pol, et al., "Refractive Index Determination of Nanoparticles in Suspension Using Nanoparticle Tracking Analysis", Nano Letters, 2014, vol. 14, pp. 6195-6201.

Van Manen, et al., "Refractive Index Sensing of Green Fluorescent Proteins in Living Cells Using Fluorescence Lifetime Imaging Microscopy", Biophysical Journal: Biophysical Letters, Jan. 16, 2008, 3 pages.

Zijp, F., "Near-Field Optical Data Storage", Koninklijke Philips Electronics N.V., 2007.

\* cited by examiner

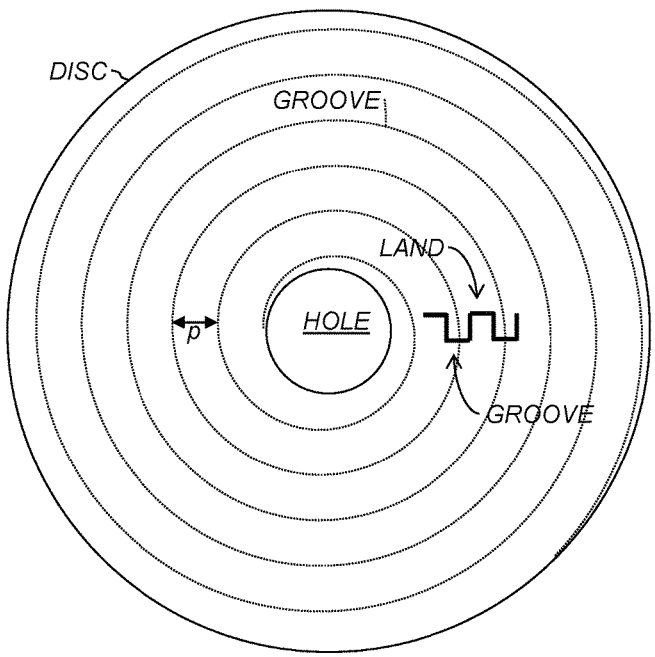
FIG. 2
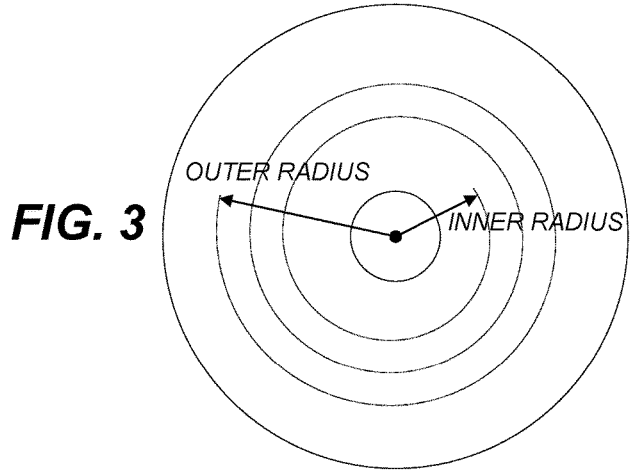
FIG. 3
FIG. 4
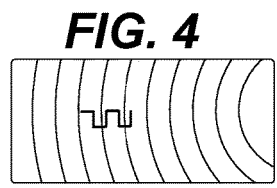
FIG. 5
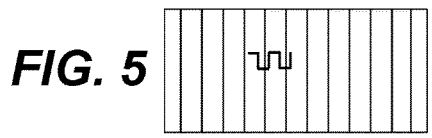

US 10,060,850 B2

PARTICLE DETECTION USING REFLECTIVE SURFACE

CROSS-REFERENCE TO RELATED APPLICATIONS

The present application is a national stage application of International Patent Application No. PCT/US2016/025650, filed Apr. 1, 2016, which claims priority to, and the benefit of, U.S. Provisional Patent Application Ser. No. 62/142,818, filed Apr. 3, 2015, and entitled "Particle Detection Using Reflective Phase Grating", and U.S. Provisional Patent Application Ser. No. 62/211,452, filed Aug. 28, 2015, and entitled "Photon Detection", the entirety of each of which is incorporated herein by reference.

BACKGROUND

Various techniques are used for investigation of microscopic particles. For example, electron micrographs can be taken of nanostructures in vacuum. Brownian motion due to microparticles in a suspension can be detected. Flow cytometers can be used to detect light scattered by nanoparticles. However, these techniques are not suitable for, e.g., clinical diagnostic testing.

BRIEF DESCRIPTION OF THE DRAWINGS

Features and advantages of various aspects will become more apparent when taken in conjunction with the following description and drawings. Identical reference numerals have been used, where possible, to designate identical features that are common to the figures. The attached drawings are for purposes of illustration and are not necessarily to scale.

FIG. 2 shows an example LOC in a disc format having a spiral track.

FIG. 3 shows an example LOC in a disc format having a spiral track.

FIG. 4 shows an example plan view of grooves on an example LOC.

FIG. 5 shows an example plan view of grooves on an example LOC.

DETAILED DESCRIPTION

Overview

Figure 1:
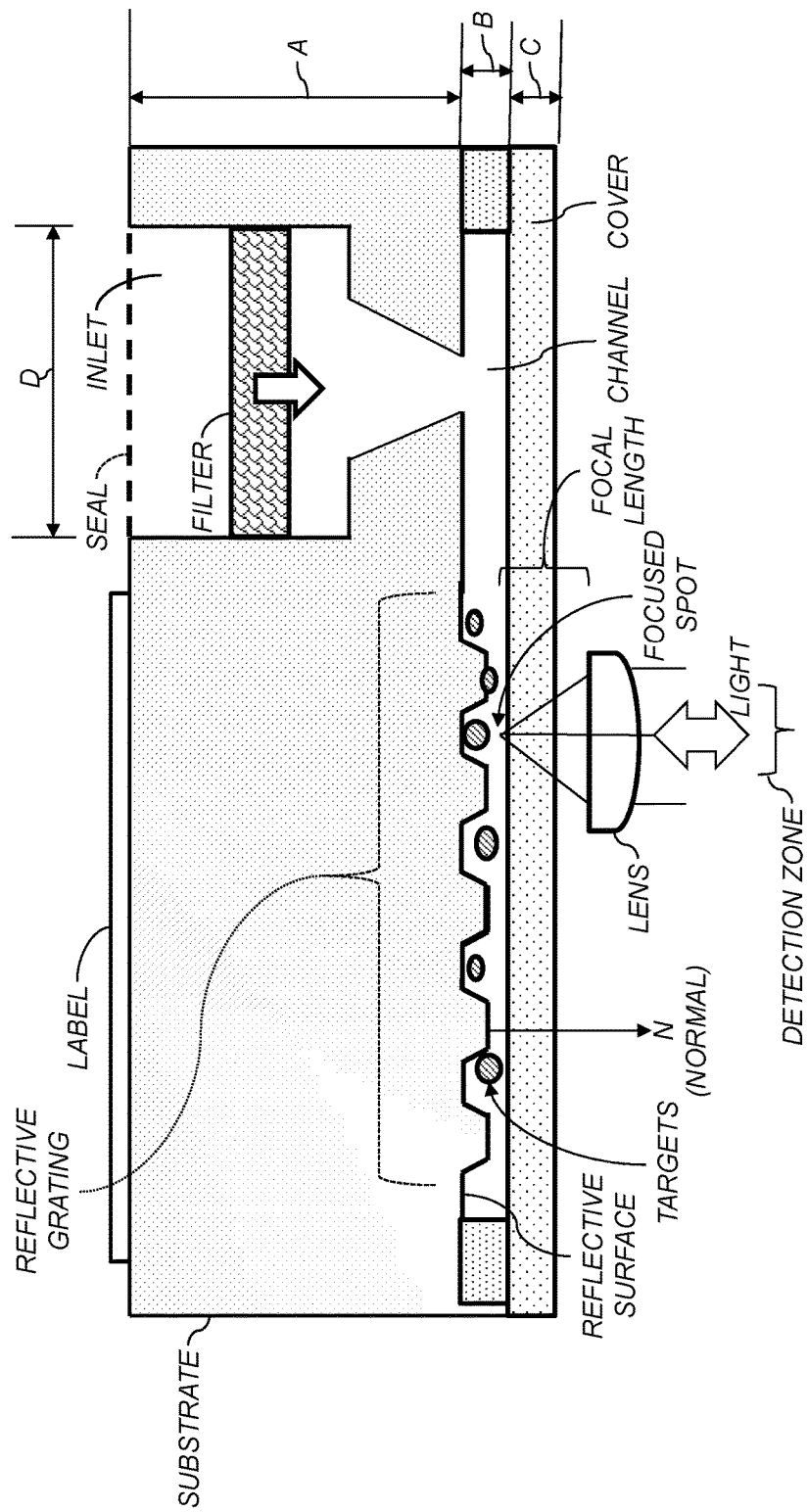
FIG. 1 shows an elevational cross-section of an example lab-on-chip device (LOC) and related components.

In the fields related to life sciences such as genetics, immunology, molecular biology, and environmental science, optical techniques are widely used to analyze microparticulate samples such as living cells, yeast, and bacteria. For example, particles or cells from 500 nm up to 50 μm can generally be measured in flow cytometry. In some examples, a label made of a fluorescent substance is attached to the surface of a cell to be analyzed. Next, laser light is radiated towards a predetermined position to irradiate the cell. Then, forward-scattered light and side-scattered light, which are generated due to the size and structure of each cell, and fluorescence, which is generated by excitation due to the light irradiation, are observed. In the case of observing fluorescence from a cell, a configuration for spectral analysis of the fluorescence condensed in a direction other than an irradiation path of excitation light is widely used to avoid adverse effects of transmitted or scattered excitation light. Fluorescent substances to be attached or combined for each type of cells are known. Accordingly, the wavelength and intensity of the fluorescence are observed and the intensity component to be superimposed is compensated to thereby identify the type of each cell.

There is a need for detecting and measuring sub-structures within cells or produced by cells. For example, cells can produce or receive "vesicles" or "microvesicles," lipid bilayers surrounding proteins, DNA, RNA, mRNA, miRNA, proteins, cytotoxins, waste from metabolic processes, or other components of a cell or substances that can be found within a cell. Vesicles can be, e.g., 4 nm-8 μm, or 100 nm-1 μm, in mean diameter. Some example vesicles include protein-enriched micro-vesicles. By "protein-enriched micro-vesicle" is meant a fusogenic structure that includes an amount of one or more target proteins in a lipid bilayer envelope. As used herein, the term "fusogenic" refers to the property of the micro-vesicle which provides for the fusion of the membrane of the micro-vesicles to the membrane of the target cell. Fusogenic micro-vesicles are capable of fusion with the lipid bilayer membrane of a target cell to deliver their contents, e.g., the target protein(s), into the cell. As used herein, a "target" can be a microvesicle or other microparticulate structure to be measured. As used herein, a "sample" can be a solid, liquid, or gaseous aggregate of one or more targets. A sample can additionally include non-target substances. For example, a blood sample can include microvesicle targets and plasma; the plasma in this example is a non-target substance. In other examples, the sample can include water and the targets can be suspended in the water. In still other examples, the sample can include a resist, solvent or other chemical used in semiconductor fabrication, or other chemical, and the target can include a nanoparticle or particulate used in industrial applications. Some examples permit measuring targets, e.g., nanoparticles, having sizes below the diffraction limit of prior flow-cytometry systems.

Various aspects relate to a quantitative microvesicle (MV) measurement platform. Some examples use a focused light spot, e.g., a scanning laser spot, on a reflective surface. The reflective surface can include a grating, e.g., a reflective grating. The terms "optical" and "light" are not limited to the visible range of, e.g., 400 nm-700 nm unless otherwise expressly specified. The term "reflective" can describe, but does not require, 100% reflection in any particular wavelength band.

Some example targets can include microvesicles, which can be intracellular or extracellular. Extracellular vesicles (EVs) can include, e.g., substantially spherical EVs having diameters between 30 nm and 1000 nm; tubular or other substantially elongated EVs between 1 μm and 5 μm in size; or EVs between 4 nm and 500 nm in size. Example targets can include high-density lipoprotein (HDL) EVs of ~10 nm in size or low-density lipoprotein (LDL) EVs of ~22 nm in size. Other targets can include large fragments up to about 8 μm in size.

In some examples, microvesicles can be present in human blood plasma in concentrations from $10^4$-$10^{12}$ per mL. In some examples, over 80% of vesicles in a sample can have diameters less than 100 nm. Vesicles can have an index of refraction n, e.g., of about 1.40, compared to silica at n≈1.45 and polystyrene at n≈1.61. In some prior flow-cytometry schemes, microvesicles such as liposomes having diameters≈100 nm can be difficult to distinguish from threshold noise in the system.

A quantitative measurement platform, e.g., for microvesicles, can provide nanoparticle detection on reflective phase grating implemented using a focused scanning laser spot on a reflective phase grating in a microfluidic channel. Various examples of such measurement platforms, systems, and techniques are discussed below with reference to FIGS. 2-31. Various examples of simulated and measured data are described below with reference to FIGS. 20, 21, and 29-33.

Various example techniques and systems described herein can provide quantitative measurements of particles, e.g., 10 nm-1000 nm in mean diameter. 10 nm is beyond the resolution of many prior optical detection systems. Some prior schemes for high-resolution imaging or particle detection include electron microscopes, Brownian-motion detection of particles in suspension (e.g., NANOSIGHT), and flow cytometry. However, although some electron microscopes may be able to observe 10 nm targets, electron microscopes are unable to observe living cells or cell components such as vesicles since electron microscopy involves drying the sample and placing it in a vacuum chamber. Moreover, scattering measurements from flow cytometers often cannot detect particles smaller than the diffraction limit at a particular wavelength, e.g., smaller than about 500 nm.

Various aspects herein permit measuring targets, e.g., small particles or structures such as vesicles or nanoparticles. Various aspects permit performing such measurements without damaging living cells or microorganisms that are being measured or the area producing the targets being measured, e.g., a living cell. Various aspects can provide quantitative measurements of targets. Various aspects can be used in a clinical environment as a disposable chip or disc (individually or collectively a "lab on chip" or LOC, whether in chip format or otherwise) including sample preparation/processing/target measurement/disposal, e.g., without the need for free liquid reagents or suspensions. Various aspects use fluorescence to further measure properties of specific targets. Example targets can be substantially equal to, e.g., 100 nm, 70 nm, 50 nm, or 30 nm in diameter. Targets having other diameters can also be measured.

Various aspects include diffraction detection of targets on reflective phase grating structures. Such structures can provide double phase modulation of light traveling through the targets. Various phase gratings provide a microscopic reference scale of sinusoidal signal characteristics.

Some examples herein provide quantitative measurement method of micro vesicles or any kind of nanoparticles, e.g., in solution. Some examples herein permit clinical testing, e.g., using closed system in a disposable chip or disc format. Example LOCs can include sample preparation, processing, and disposal in a single LOC. Some examples herein permit identifying the origin of detected microvesicles, e.g., using fluorescent tagging.

Some examples provide detection of a particle on a reflective surface, e.g., a substantially flat reflective surface such as a mirror, by detecting light absorption or refraction due to a target. Some examples provide diffraction detection of a particle on a reflective phase grating structure, which structure can double the phase modulation sensitivity of a detection system. The phase grating can provide a microscopic reference scale against which targets can be measured. Some examples use a phase grating having a height or depth, e.g., substantially equal to $\lambda/8n$, e.g., 40 nm, or substantially within the range $\lambda/16n$-$3\lambda/16n$, where $\lambda$ is a wavelength of incident optical radiation and n is a refractive index of the medium, e.g., a fluidic sample. This configuration can provide higher amplitude or improved signal-to-noise ratio (SNR) of push-pull signals. In some examples, $\lambda\approx405$ nm, NA≈0.85, and a cover having a thickness of about 0.1 mm is placed over the sample. In some examples, relatively shorter wavelengths or relatively higher numerical apertures (NAs) can be used to detect relatively smaller particles. In some examples, $\lambda\geq\sim405$ nm can be used with polymer disposable LOCs.

In some examples, a reflective phase grating can be used and a focused scanning laser spot can be applied. In some examples, an LOC can have a disc or rectangular style (e.g., slide glass) format.

Illustrative Examples

FIG. 1 shows example of a lab-on-chip device (LOC). The LOC is an example of a sample carrier, a device for retaining or transporting a sample for measurement as described herein. In some examples, as graphically represented by the double-headed "light" arrow, a target in a detection region is irradiated by a focused spot of light. The focused spot of light can have a range of irradiation wavelengths, of which the peak power, or mean, median, or other representative wavelength can be an irradiation wavelength. Resultant light is detected concurrently with or subsequent to irradiation. Resultant light can include, but is not limited to, light reflected by the target, light emitted by the target, or light reflected or diffracted by a reflective surface, e.g., a reflective grating, in the detection region. References herein to detecting or measuring resultant light can include producing signals, e.g., analog or digital electrical signals, representing at least some of the resultant light, unless expressly indicated.

In some examples, dimension A can be ~1.1 mm, dimension B can be ~1 μm or ~2 μm, dimension C can be ~100 μm, or dimension D can be ~500 μm. In some examples, a reflective surface, e.g., a reflective grating, can be directly overcoated with a layer, e.g., a clearcoat protective layer. Targets, e.g., in a fluid sample, such as a liquid sample, can be deposited onto the reflective layer or the clearcoat layer for measurement.

Figure 8:
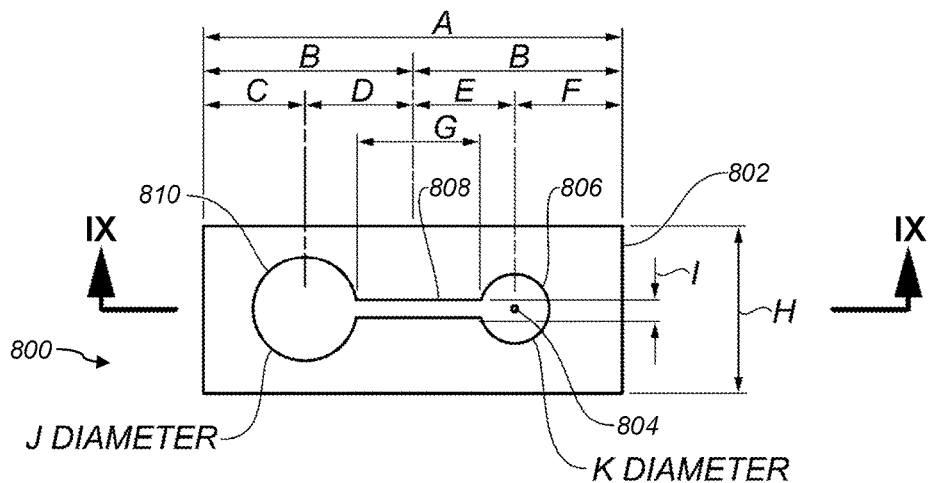
FIG. 8 shows a plan-wise cross-section of an example LOC.

The fluid sample can be added through a sample inlet ("INLET"), e.g., after removing a seal ("SEAL"). The inlet can be associated with a substrate of the LOC, e.g., can be arranged in, on, over, or through the substrate. The inlet can include or be associated with a filter ("FILTER"). The inlet can convey at least some of the fluid sample, e.g., in the direction indicated by the open arrow, to a fluid channel ("CHANNEL") configured to convey at least some of the fluid sample towards (e.g., over) the reflective surface. The reflective surface can be associated with the substrate of the LOC, e.g., can be arranged on, in, or over the substrate. The sample inlet can be fluidically connected to the channel. As used herein, components that are "fluidically connected" are structured and arranged to permit a relevant fluid to flow between them. Fluidically connected components can be directly connected, or can be connected via intermediaries (e.g., as inlet area 806 and 810, FIG. 8 are fluidically connected via fluid channel 808, as discussed below).

Table 1 lists attributes of sample carriers according to various examples herein. This disclosure expressly contemplates each possible combination of attributes formed by selecting one attribute value from each row of Table 1. Sample carriers can include, e.g., disc, slide, or chip formats, as described herein.

TABLE 1

| Category | Attributes |
| --- | --- |
| Reflective Surface | "Mirror" (substantially flat); grating |
| Cover between optics and sample | Present; absent |

TABLE 1-continued

| Category | Attributes |
| --- | --- |
| Cover material | Glass; plastic |
| Target carrier | vacuum; air; dried formerly-liquid sample; stationary liquid; flowing fluid |
| Target type | Homogeneous refractive index; heterogeneous refractive index |
| Material between reflective surface and target | Present; absent |
| Format | Disc; slide; chip |

In addition, this disclosure expressly contemplates detecting resultant light, e.g., light reflected by or emitted from or over a sample carrier having any combination of attributes listed in Table 1. This disclosure expressly contemplates detecting such light using detection systems such as those listed in Table 2, e.g., using respective systems according to each possible combination of one attribute value per row. That is, any selection of one attribute per row of Table 1 can be combined with any selection of one attribute per row of Table 2. In Table 2, "focusing" refers to adjusting spot position substantially normal to a sample carrier, and tracking refers to adjusting spot position substantially laterally with respect to a sample carrier, e.g., to track a groove such as those shown in FIGS. 2-7.

TABLE 2

| Category | Attributes |
| --- | --- |
| Emission wavelength | Ultraviolet; visible; infrared |
| FWHM | Specific values for, e.g., Gaussian or flat-top profiles (see, e.g., Table 3) |
| Numerical aperture | Specific value (see, e.g., Table 3) |
| Type | Laser; collimated beam |
| Focusing | Present; absent |
| Tracking | Present; absent |
| Detection wavelength | Substantially the same as an emission wavelength; substantially different from an emission wavelength or from any emission wavelengths |
| Motion | Stationary irradiation spot; moving irradiation spot |

Examples of specific attribute values are shown in Table 3. This disclosure expressly contemplates using any of the attribute values shown in Table 3, or any combination thereof, with any combination of corresponding attributes listed in Table 1 or Table 2. In some examples, the emission wavelength can be, e.g., an irradiation wavelength as described herein. The emission wavelength can be selected to excite fluorescent emissions from a target, though this is not required. Fluorescence is described herein with reference to, e.g., FIG. 13-15, 19, or 26.

TABLE 3

| Category | Attributes |
| --- | --- |
| Cover material | Polycarbonate; glass |
| Target carrier | Flowing liquid; flowing gas |
| Material between reflective surface and target | A spin-coating over a reflective grating; a glass or plastic slide having the reflective material on the opposite side from the surface that receives the sample. |
| Format | A microscope slide having a reflective coating; a fluidic chip including a flow cell, flow chamber, or other flow channel. |
| Emission wavelength | 785 nm; 650 nm; 405 nm |
| FWHM | 1040 nm; 557 nm; 245 nm |
| Numerical aperture | 0.45; 0.60; 0.85 |
| Focusing | Using a lens to focus a laser beam on a flow channel |
| Detection wavelength | The wavelength of fluorescence of a dye added to the sample to indicate presence of targets |
| Motion | A substantially stationary irradiation spot used with a flowing fluidic sample; a moving irradiation spot scanned, e.g., raster-scanned or scanned linearly, across a flow channel. |

FIG. 2 shows an example disc (the spellings "disk" and "disc" are interchangeable herein) with a hole in the center. A spiral track, e.g., a land or groove, is shown dotted and has a fixed pitch p across the surface of the disc. "Lands" include non-recessed or raised areas; "grooves" include recessed or lowered areas (or non-raised areas, in examples including raised lands). Shown superimposed on the spiral in heavy lines is a cross-section. In the illustrated example, the track follows grooves that are separated by lands of the same widths as the grooves. In this example, the track does not have pits and lands burned along the length of the track as a data-bearing BLU-RAY disc does. In other examples, the track includes some data-bearing areas. In some examples, a single disc carries data-bearing tracks and non-data-bearing tracks. Various examples of reflective phase gratings are discussed and shown herein, e.g., the groove in FIG. 2. However, the orientation(s) of grooves or lands in a reflective phase grating and the orientation(s) of laser spot travel (if any) are not constrained. In some examples, the laser spot moves substantially radially rather than substantially tangentially or substantially along a spiral. As used herein, the term "disc" does not require that the disc be perfectly circular. For example, a disc-format LOC can include a disc trimmed to fit within a rectangle, as for business-card sized CD-ROMs having two shorter, rounded edges and two longer, straight edges.

FIG. 3 shows an example disc in which the track does not extend across the full radius of the disc. The track covers a portion of the disc between an inner radius and an outer radius. Multiple tracks can be arranged in different radial zones of the disc. Multiple tracks can be interleaved, e.g., starting from the same radius but 180° around the disc from each other.

LOCs, e.g., in disc format, can be manufactured having desired numbers of tracks, track pitches, radii, interleaving, groove width, land width, or orientation, using CD, DVD, or BLU-RAY duplication technology. The pitch of the tracks can be selected based on the size of the targets to be detected. A single LOC can include multiple regions, spaced apart or overlapped. Each region can have a respective groove pitch, depth, or pattern, the same as or different from at the pitch, depth, or pattern of at least one other region, respectively. For example, a disc-format LOC can include two spaced-apart concentric spiral grooves, one having a relatively narrower pitch (e.g., for detecting relatively smaller particles) and one having a relatively wider pitch (e.g., for detecting relatively larger particles).

In some examples, the negative pattern of the lands and grooves of the track can be transferred to a stamper, e.g., made of nickel. The stamper can be positioned with respect to an injection mold so that polycarbonate (PC) or another material injection-molded in that mold takes on the desired pattern of lands and grooves. The molded polycarbonate can then be sputter-coated, e.g., with aluminum or silver, e.g., ~18 nm, ~20 nm, ~50 nm, or ~100 nm thick, to form a reflective surface that can be read by a laser. Compared to a relatively thinner reflective surface, a relatively thicker reflective surface can, e.g., have increased reflectivity, exhibit reduced autofluorescence (AFL); or experience reduced thermal damage during measurement. Increased reflectivity or reduced AFL can increase measurement sensitivity, and reduced thermal damage can increase lifetime of a sample carrier. In some examples, the reflective layer can be, e.g., overcoated with a transparent thin-film hard-coat. In some examples, the reflective layer can comprise, e.g., anodized Al or another anodized substance.

In some examples, phase transition mastering (PTM) can be used to manufacture the stamper. PTM involves developing the desired pattern in an inorganic photoresist over a silicon wafer. The wafer can then be etched to prepare the stamper.

In some examples, laser writing such as used in dye-based recordable DVDs can be used to manufacture discs. The desired pattern of grooves can be burned into a dye layer of such a disc using a laser.

Above-described manufacturing techniques for discs can be used to prepare spiral tracks or other shapes or groove or pit patterns in non-circular substrates, e.g., substantially quadrilateral (e.g., rectangular) shapes used for lab-on-chip devices (LOCs). These devices can be scanned with focused laser light, as described herein. LOCs, e.g., in disc or chip format or other formats described herein, can be reusable or disposable. For example, a single reflective grating can be repeatedly washed and reused for each of multiple samples in succession, or multiple gratings can be used for respective samples tested in succession. As used herein, the term "focused spot" and similar terms refer to a spot produced by an irradiation system configured to focus the spot to a desired extent on a surface. The term "focused spot" does not constrain the tolerances of components of the irradiation system or other systems herein.

One or more portions of a disc or other LOC can have respective groove patterns (e.g., spiral, straight, concentric circles, or other curves). Different portions can have different patterns or the same pattern, in any combination. In an example, at least two portions of a disc-shaped LOC have spiral groove patterns with different pitch values (p). This can permit effectively detecting targets in different size ranges. A LOC (disc or otherwise) can have one or more sample inlets, vacuum outlets (e.g., ports or channels to which vacuum can be applied to move sample), or one or more detection regions. Example LOCs according to various aspects are described herein with reference to in FIGS. 1-10 and 16. For example, the grooves can have a depth of 40 nm and a pitch of, e.g., ~500 nm (e.g., 250 nm or 250.5 nm width for the grooves or the lands).

FIG. 4 shows an example plan view of spiral grooves, e.g., forming a reflective phase grating, e.g., on an LOC such as a rectangular LOC. As in FIG. 2, the groove profile is represented by the cross-section in heavy lines.

FIG. 5 shows an example plan view of straight grooves, e.g., forming a reflective phase grating, e.g., on an LOC such as a rectangular LOC. As in FIG. 2, the groove profile is represented by the cross-section in heavy lines.

Figure 6:
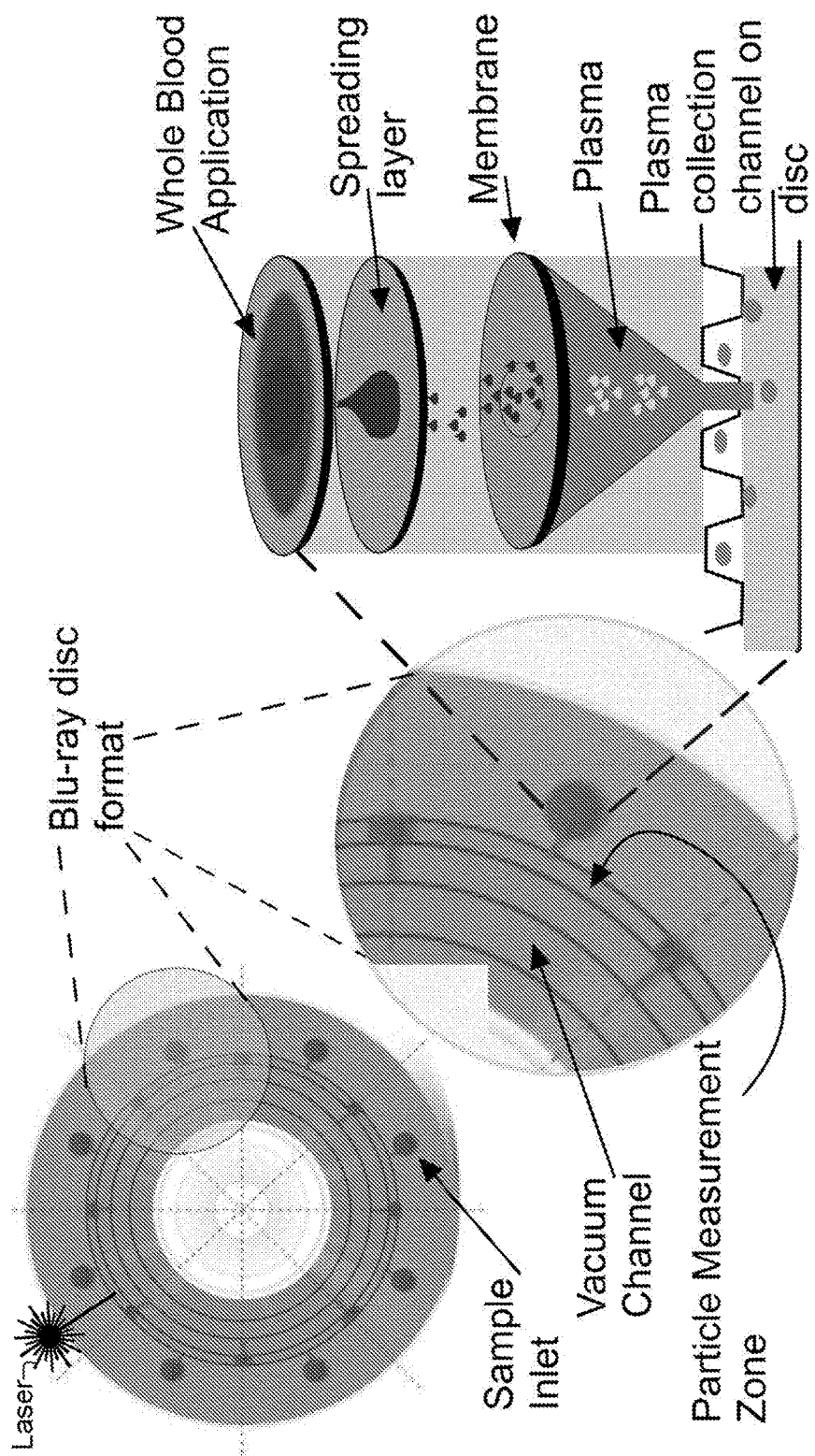
FIG. 6 shows components of an example LOC in a disc format and configured, e.g., for analysis of blood samples.

FIG. 6 shows an example disc and filter system configured for separation of plasma containing microparticles, e.g., microvesicles. The illustrated filter system can alternatively be used with other configurations of LOC or reflective grating, e.g., glass slides. Samples can flow through channels in the LOC, e.g., due to vacuum pressure via the illustrated vacuum channel, due to capillary force (e.g., in air, in vacuum, or in another atmosphere), or due to other forces.

Any number of sample inlets, vacuum channels, or detection regions (e.g., measurement zones) can be used. Vacuum can also or alternatively be applied via vacuum ports. Samples or vacuum can be applied before or during relative motion of the laser spot and disc. Capillary channels, e.g., micropillar channels, or other features can be used to draw sample into the detection regions.

Micropillars, inlets, channels, ports, and other features shown can be formed using stampers in an injection mold, e.g., as for the reflective phase grating, or can be formed using etching, machining, or other techniques. Multiple layers of a disc or other LOC can be prepared separately and affixed, or layers can be built up or formed together or one after another, in any combination.

Any number of the, e.g., eight samples can be applied substantially simultaneously, or at different times. Any number of samples can be measured in a single rotation of the disc or other single laser pass across the reflective phase grating, or in multiple passes, in any combination.

Figure 7:
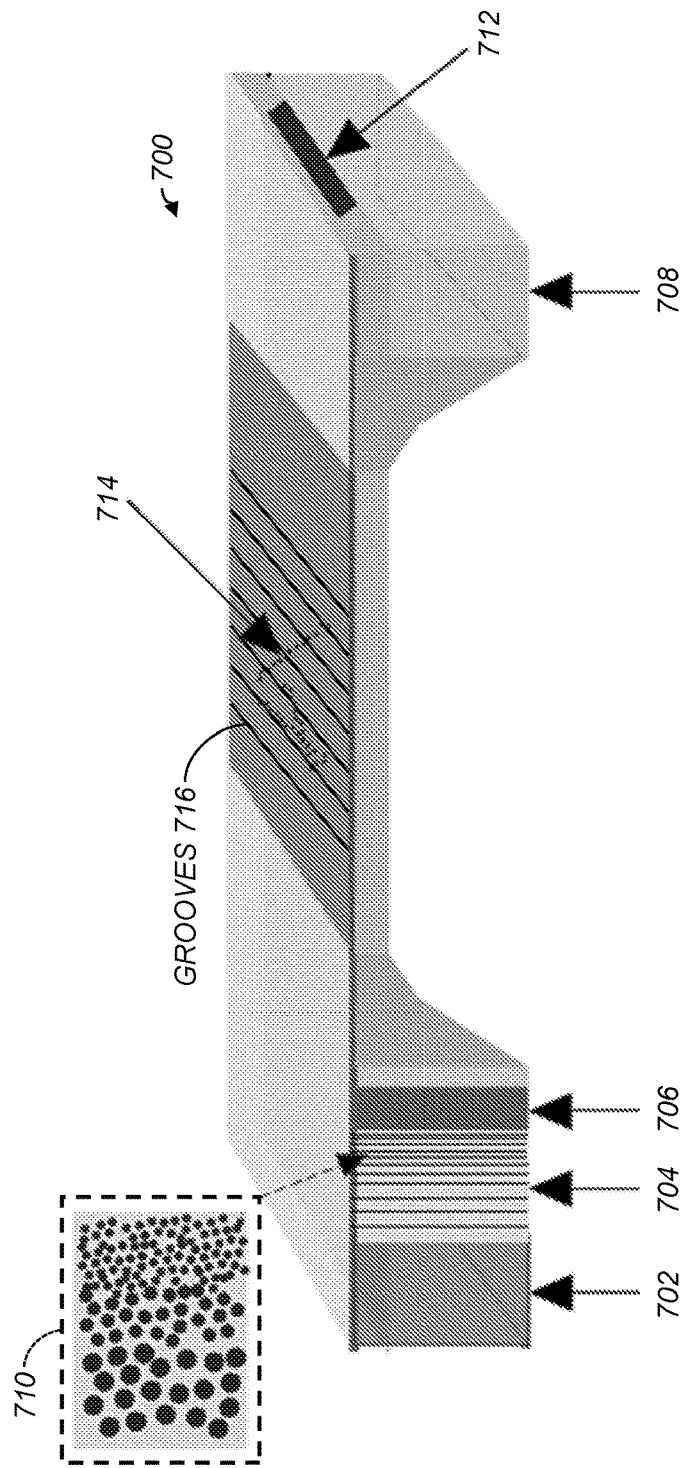
FIG. 7 shows a perspective and partial cross-sections of components of an example LOC, and example groove patterns.

FIG. 7 shows another example of an LOC 700. In some examples, LOC 700 includes multiple fluid tanks, e.g., four tanks 702, 704, 706, and 708 (or three tanks 702, 704, and 708, or any combination of any number of the four tanks). For example, tank 702 can include a 20 μL tank to which sample, e.g., blood, is added, e.g., through the top, end, or side of LOC 700 or tank 702. Tank 704 can include cell-separation or other filtering features, e.g., micropillars. An example micropillar arrangement is shown in plan in inset 710, with arrows indicating the direction of sample flow. In some examples, tank 706 can hold dye(s) or other substances to enhance optical detection of targets. Tank 708 can be, e.g., a reservoir or waste tank. In some examples, tank 708 can include an outlet 712, e.g., configured to connect to a vacuum source.

In detection region 714, targets (illustrated as dots) can be irradiated. Resultant light from detection region 714 can be detected. Detection region 714 can include grooves 716, graphically represented as lines.

In various examples, a disc or other LOC can have lands L between grooves 716 of depth Dg. Targets can be in the grooves or on the lands. In some examples, the groove depth Dg is substantially equal to $\lambda/8n$ to increase magnitude of the tangential push-pull (PP) signals from the phase grating. In some examples, the track pitch p is set to at least twice the size (e.g., mean diameter) of targets to be detected. In some nonlimiting example configurations of grooves 716, an individual groove 716 can be straight or curved, or can have both straight segments and curved segments. The grooves 716 can be connected, e.g., as part of a spiral, or can be separate. An individual groove 716 can have a substantially constant cross-sectional profile (e.g., depth, width, and area), but this is not required.

FIG. 8 shows a plan-wise cross-section of an example LOC 800 having a substrate 802, e.g., including glass or polymer. A sample inlet 804, e.g., a hole in a cover over the substrate, is fluidically connected to inlet area 806. Inlet area 806 is fluidically connected to fluid channel 808, which can be or include a detection region in some examples. Fluid channel 808 is fluidically connected to reservoir 810. In some examples, fluid can flow from sample inlet 804, through inlet area 806, fluid channel 808, and into reservoir 810, e.g., under capillary pressure.

Figure 9:
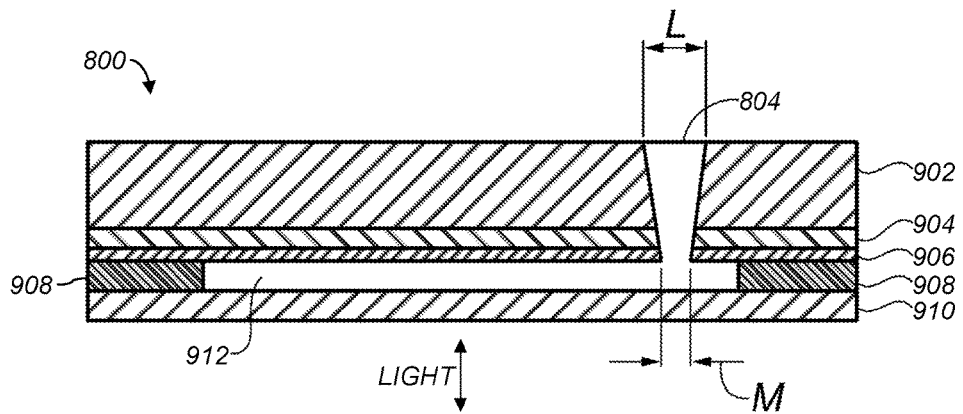
FIG. 9 shows an elevational cross-section along the line IX-IX in FIG. 8.

FIG. 9 shows an elevational cross-section of example LOC 800 along the line IX-IX in FIG. 8. Sample inlet 804 in this example is a through hole formed in a substrate 902, e.g., glass such as non-alkali glass. The substrate 902 can have a thickness of, e.g., 0.7 mm. Through-hole sample inlet 804 in this example also passes through a reflective layer 904 and oxide layer 906. Oxide layer 906 can represent, e.g., an electrically insulating layer. Reflective layer 904 can, e.g., comprise aluminum or another metal. Reflective layer 904 can have a thickness of, e.g., ~18 nm, ~20 nm, ~100 nm, or ~200 nm. The illustrated reflective layer 904 is substantially flat; however, this is not limiting. A reflective grating such as described herein with reference to FIGS. 1-7 can be used as or in place of at least part of the reflective layer 904. Oxide layer 906 can, e.g., comprise $SiO_2$. Oxide layer 906 can have a thickness of, e.g., 15 nm. Spacers 908 separate the oxide layer 906 from a cover 910, thereby defining a channel 912. Spacers 908 can comprise, e.g., resin. Spacers 908 can have a thickness of, e.g., 1 μm. Cover 910 can comprise, e.g., glass, such as non-alkali glass. Cover 910 can have a thickness of, e.g., 0.1 mm. Targets in channel 912 can be irradiated through cover 910, and resultant light can pass through cover 910 back to a detection system, as represented by the double-headed "LIGHT" arrow.

In FIGS. 8 and 9, in some nonlimiting examples, the illustrated dimensions can be as shown in Table 4. In addition, sample inlet 804 can have a diameter of 0.5 mm. Sample inlet 804 is shown tapered in FIG. 9, but can alternatively have a substantially constant diameter.

TABLE 4

| Label | Example Value (mm) |
| --- | --- |
| A | 25.0 |
| B | 12.5 |
| C | 5.5 |
| D | 7.0 |
| E | 6.0 |
| F | 6.5 |
| G | 8.0 |
| H | 10.0 |
| I | 1.0 |
| J | 6.0 |

TABLE 4-continued

| Label | Example Value (mm) |
|---|---|
| K | 4.0 |
| L | ≥0.5 |
| M | 0.5 |

Various examples permit measuring a small number of microparticles, e.g., one microparticle at a time. Some examples use a flow cell and a small spot to illuminate one particle at a time in the spot. For example, a flow cell having dimension I (channel 808 width) of approximately 1 µm can provide a microvesicle concentration of ~10 µm×10 µm area per particle. A 0.4-µm spot can be used. These parameters can provide individual measurement of one particle in a spot at a time. By contrast, some prior flow cells and optics illuminate 800-1000 microvesicles at the same time. This can make it difficult to distinguish individual particles and fluorescence thereof. Some prior schemes dilute samples ~1000×, but this can reduce microvesicle concentration to 1/100 µm$^3$, making it difficult to measure the microvesicles. Some examples herein do not have these limitations. Some examples can use a channel width (e.g., dimension I) of 2 µm or 2 mm.

Figure 10:
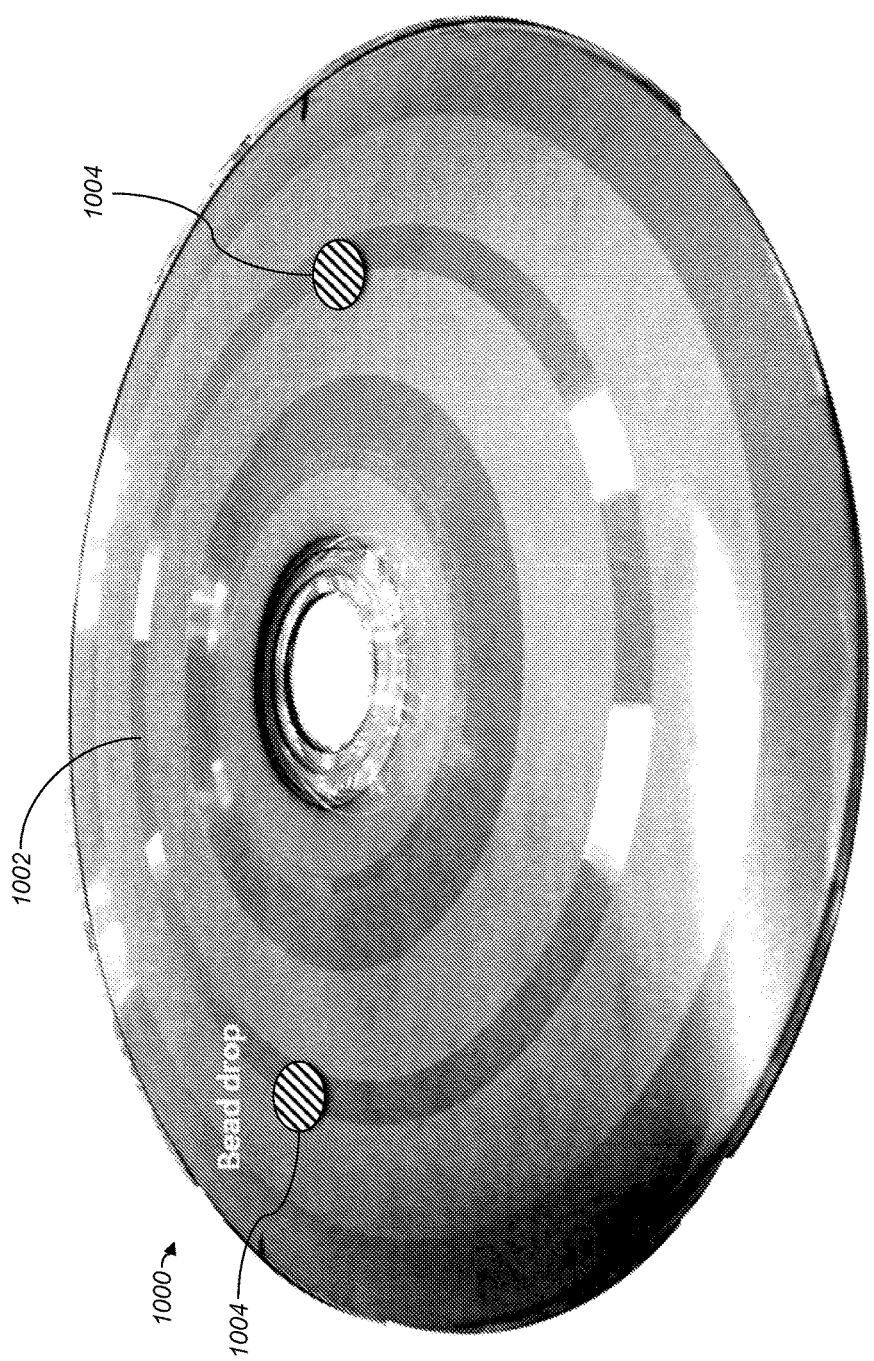
FIG. 10 shows an annotated graphical representation of a photograph of an example LOC in a disc format.

FIG. 10 shows an annotated graphical representation of a photograph of an example LOC 1000 that was prepared in a disc format. An optical disc was prepared from a customized master having a track pitch p=500 nm. The master was prepared with phase transition mastering (PTM). A nickel stamper was manufactured and the test disc was injection molded and stamped with the master. Injection molding of transparent polycarbonate was performed, then the polycarbonate was cooled, then aluminum was sputtered over the polycarbonate.

In the depicted constructed example, the disc had a single spiral groove 1002 recessed below the majority of the surface of the disc. The groove was arranged between an inner radius of 38 mm and an outer radius of 42 mm. The portions of the disc not bearing a groove are referred to as a "mirror" herein. The term "mirror" does not require that the referenced reflective surface be perfectly flat or planar. Concave or convex mirrors can additionally or alternatively be used, provided that the reflective surface is substantially flat over areas at least twice the mean size of the targets to be measured. In some examples, the reflective surface can comprise at least a section curved in order to affect the particle distribution on the reflective surface in a desired manner. The groove can be arranged relatively farther from the objective lens during measurement; the land can be relatively closer to the objective lens. The relative widths of the lands and grooves, e.g., shown in the cross-section in FIG. 2, can be substantially equal or can be different. Examples using equal land and groove widths can provide improved push-pull signal SNR. Regions 1004 ("Bead drop") are discussed below.

Figure 11:
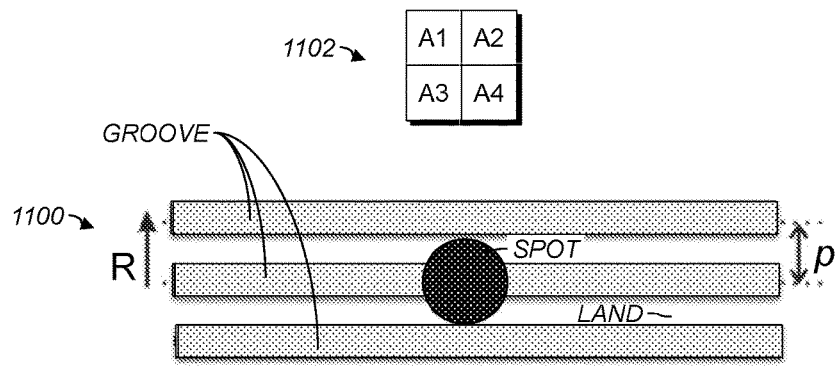
FIG. 11 shows a schematic plan view of an example reflective grating, and example measurement techniques.

FIG. 11 shows example measurement techniques. An LOC 1100 (or other substrate) is irradiated by a spot, e.g., a laser spot. The laser spot can scan or move relative to the LOC, e.g., via motion of the spot or via motion of the LOC such as rotation of a disc-format LOC, other LOC, or other substrate. As used herein, descriptions of LOC embodiments can apply to disc or other LOC configurations. A radial direction R and a groove pitch p are shown. The laser spot can track at a fixed radial position or a fixed radial rate ("no tracking"), or can be controlled to follow a land ("on-land" tracking) or a groove ("in-groove" tracking). In the illustrated example, the spot follows the groove. In some examples, e.g., of a rectangular LOC such as one shaped like a standard glass microscope slide, the spot can be scanned, e.g., rasterized, across the LOC, e.g., using galvos or polygon scanners. In some examples, e.g., of a disc-format LOC, the disc can be rotated, e.g., while moving the spot radially to track along a groove or land.

A four-way split photodetector 1102 (or two two-way split photodetectors orthogonal to each other, or another arrangement of quadrant photodetectors, e.g., a split photodiode or photodiodes) detects laser light reflected off the disc in four quadrants, A1-A4. The sum of the detected light, e.g., a sum signal or aggregate signal, is referred to herein as the "HF" signal. Considering the direction of travel of the laser spot with respect to the track as a "frontward" direction, the difference between frontward and rearward halves of a split photodiode (e.g., A1+A3−(A2+A4)) is referred to as a tangential push-pull ("TPP") signal. The difference between left and right halves of a split photodiode when viewed facing frontward (e.g., A1+A2−(A3+A4)) is referred to as a radial push-pull ("RPP") signal. The radial push-pull signal indicates how closely the spot is following the track and can be used as an input to a control loop that adjusts the radial spot position to follow the track. A tracking error signal ("TES") can be determined as (A1+A2−(A3+A4))/(A1+A2+A3−A4) (RPP divided by HF). HF and push-pull ("PP") signals can both be used to detect targets. Signal-measurement techniques and track structures described in the Kuroda, Nakajima, and Nakayama patent documents submitted herewith and noted above can be used in conjunction with measurement hardware and techniques herein in various examples. In some examples, the HF signal is modulated by particles of a sufficiently large size (depending on irradiation wavelength, irradiation spot size, and grating pitch/reflectivity). The HF signal can be processed to detect larger cells and particles. Example HF and PP signals are shown in FIGS. 20, 21, and 29-33.

As used herein, TPP and RPP signals are not limited to disc-format LOCs. For example, for X-Y scanning over a chip-format LOC, TPP signals can be along the grooves and RPP signals can be across the grooves, or vice versa. For X-v scanning, i.e., scanning the spot in an X direction different from (e.g., substantially perpendicular to) a flow direction (v) of a liquid sample, TPP signals can be in the X direction and RPP signals in the v direction, or vice versa. Alternatively, TPP and RPP signals can be at an angle to grooves or flow directions, e.g., because of interactions between X scan velocity and v flow velocity in an X-v scanning configuration.

In some examples in which targets are in grooves on the LOC, in-groove tracking can be used. In some examples, on-land tracking can be used to detect large particles that may be located on lands, e.g., because they are too big to fit in the grooves. Measurements can be taken with both in-groove and on-land tracking and the results combined, in some examples.

Figure 12:
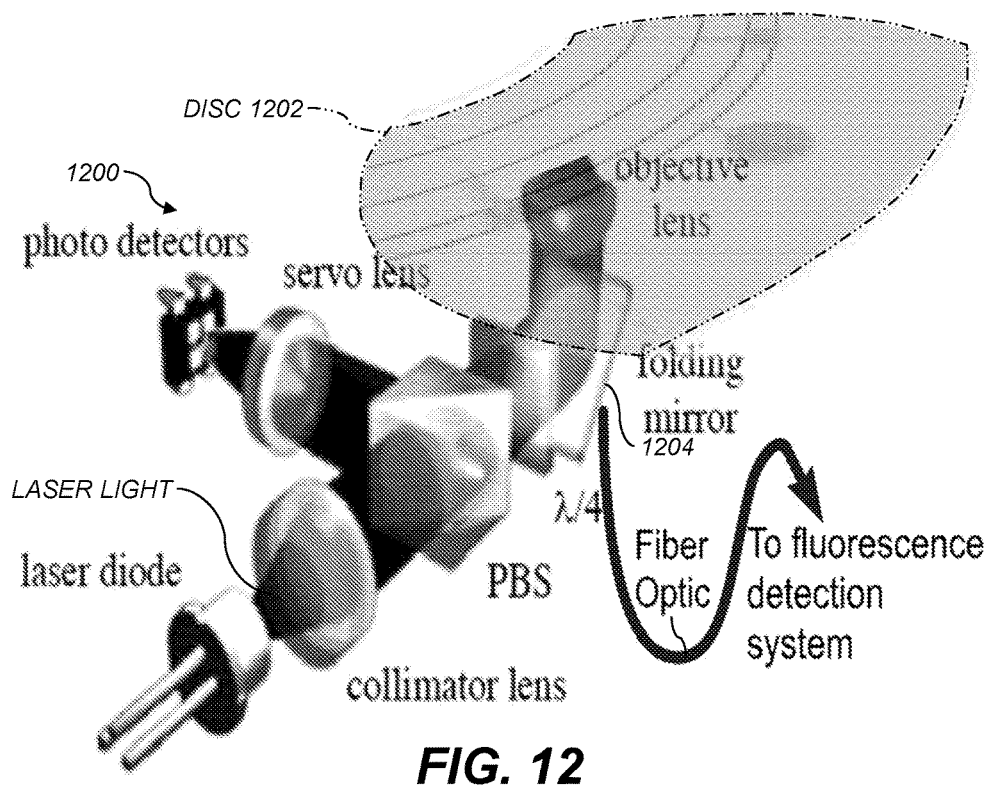
FIG. 12 shows a perspective of components of an example optical detection system, e.g., configured for detecting or measuring targets such as microvesicles.

FIG. 12 shows a perspective of example optical apparatus 1200, e.g., including a BLU-RAY optical pick up. A portion of a disc 1202 is shown in phantom for clarity of explanation. In the illustrated example, optical radiation from a laser diode strikes disc 1202. The laser light, or other light radiated onto or into the disc or other LOC (e.g., an LOC including a reflective surface such as a reflective phase grating), is referred to herein as "incident light." In some examples, the incident light can pass into or through a flow chamber, e.g., to irradiate samples or targets in the flow chamber.

Light reflected or refracted from the disc, or light emitted from samples, targets, dyes such as fluorescent dyes, or other substances in or over the disc, is referred to herein as "resultant light." In flow-chamber configurations, resultant light can include light transmitted through the flow chamber. Resultant light can include forward-scattered (FS) light and side-scattered (SS) light. FS and SS can have substantially the same wavelength as the light source does. Resultant light can also include fluorescent light, e.g., emitted by substances in or over the irradiated surface (or within the flow chamber) such as labeled antibodies. Resultant light can be, e.g., substantially directional (e.g., transmitted light of the laser light or substantially omnidirectional (e.g., fluorescence).

It is not required that all of the laser light be incident on any particular target (e.g., a microvesicle). For example, useful information can be gathered while scanning the irradiation spot over the membrane of a microvesicle, even if some of the irradiation spot is not striking the microvesicle.

In various aspects, light provided by a source other than a laser is used instead of or in addition to the laser light. The light source can be any source that can be focused to produce an irradiation spot, e.g., a diffraction-limited spot, a spot having a FWHM <2 μm, or a spot smaller than the target to be irradiated. Example sources can include, e.g., a lamp positioned at the focus of a parabolic reflector, or a light-emitting diode (LED) focused through a lens.

In an example, transmitted light or forward-scattered light can be coherent light that is affected by scattering, refraction, absorption, rotation of the plane of polarization, or other effects on the light due to the irradiation of the laser light onto the targets. In an example, the fluorescence or side-scattered light can be incoherent light. Coherent side-scatter and back-scatter light can also be detected.

In some configurations, targets are detected using outputs from the photodetectors. In the illustrated example, at least some resultant light passes back towards mirror 1204, e.g., a beam-folding mirror. In some configurations, the coating of the mirror 1204 is selected to transmit some light from fluorescent dyes in or bonded to targets. Such light can be collected by the fiber optic cable or other collection optics. In some configurations, the coating of the mirror 1204 is selected to reflect some light having a wavelength similar to that of the incident light. The illustrated polarization beamsplitter or another beamsplitter can be used to direct the resultant light having the wavelength similar to that of the incident light to, e.g., split photodetectors. In some examples, the linear velocity of a target over the objective lens is ~1 m/s. In some examples not shown, a flow cell is used that carries targets at, e.g., ~1 m/s.

In some examples using incident light at ~405 nm from the laser diode, the mirror 1204 is ~100% reflective at 405 nm. In some examples, in order to get fluorescence (fluorescent) light through mirror 1204, a coating with R405≈100% (reflectance at 405 nm) and T>405 nm≈100% (transmission at wavelengths longer than 405 nm) is applied to mirror 1204.

Figure 13:
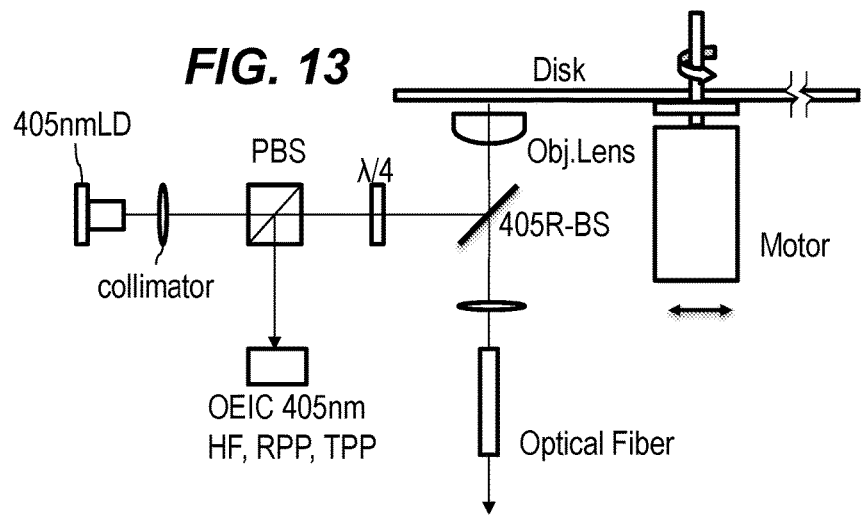
FIG. 13 shows a schematic of an example optical detection system.

FIG. 13 shows a schematic of an example optical detection system. A laser diode (LD) provides optical radiation through a polarization beamsplitter (PBS). The radiation passes through a quarter-wave plate (λ/4) and is reflected by a 405 nm-reflective beamsplitter (405R-BS). The radiation is focused by an objective lens ("Obj.Lens") onto an LOC, in this example a disc rotated by a motor. The lens and associated components, or the motor and disc, can be translated left-to-right in the figure, e.g., to track grooves. The resultant light from the LOC passes back to the 405R-BS. Fluorescent or other resultant light at a substantially different wavelength from the incident light passes through the 405R-BS to an optical fiber. Resultant light substantially at the same wavelength as the incident light passes through the λ/4 plate, is reflected by the PBS to a photodetector, e.g., an Optoelectronic Integrated Circuit (OEIC) such as an OEIC including a split photodiode and readout electronics. PMTs (photomultiplier tubes) or other optical sensors can also or alternatively be used, e.g., a PMT, avalanche photodiode (APD), or multi-pixel photon counter (MPPC). Other optical sensors can also or alternatively be used.

In some examples, the detection system and the LOC are arranged to provide a gap between the objective lens and the flow channel. In some examples, the gap is $\lambda/NA^2$, e.g., 0.56 μm for BLU-RAY optics. In some examples, the gap is ≤5 μm, or ≤2 μm, or 1 μm. Gaps <5 μm can permit moving fluid in a channel via capillary action. In some examples, the gap is $<c\lambda/NA^2$, for ~4≤c≤~8, or between ~5 μm and ~10 μm. In some examples, the channel height is ≤5 μm, or ≤2 μm, or 1 μm.

Figure 14:
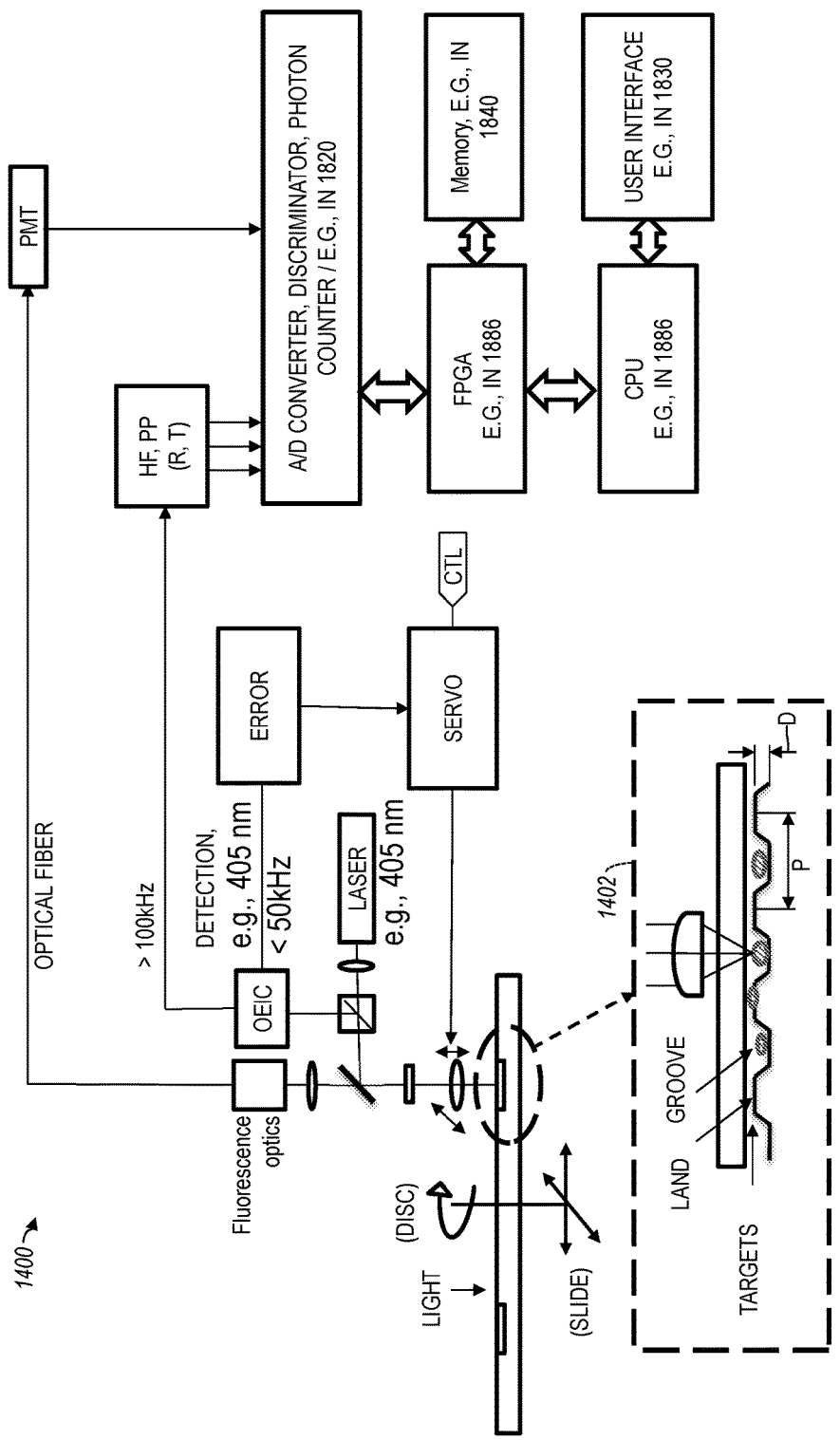
FIG. 14 shows a block diagram of an example target-measurement system.

FIG. 14 shows an example target-measurement system 1400. Details of various illustrated components are discussed herein with reference to FIGS. 13 and 15-19.

"Error" represents computation of Focus & Tracking Error Signals, e.g., as used in CD-ROM, DVD, or BLU-RAY discs. Error signals are provided to a servo drive ("servo"), which can operate a voice coil or other actuator to adjust position or orientation of one or more lenses or other optical components to maintain focus and tracking. Various aspects include separating a detected signal into servo bandwidth signals and detected particle signals. This can be done, e.g., using split photodetectors or using filters on specific temporal-frequency ranges. Examples of temporal-frequency ranges are shown as annotations on illustrated signal paths.

In some examples, the servo drive can receive control signals ("CTL") and can adjust the focus depth of the spot in response to the control signals. This can permit focusing the spot on the reflective surface or on targets, e.g., the surfaces or centers of targets. This can also permit adjusting focus to more effectively detect targets either on-land or in-groove.

In some examples, the servo drive can respond to the control signals to adjust the focal plane, e.g., within a 0.5 μm range. This can permit scanning a volume, e.g., of a groove or flow channel. Volume scanning can in turn permit reducing double-counting of targets, or increasing accuracy of target scanning when the targets are moving.

Actuators (omitted for brevity) can rotate ("(DISC)") or translate ("(SLIDE)") the LOC or other sample carrier, in conjunction with or independently of motion of the irradiation spot, to permit scanning the spot across a sample as discussed herein.

Inset 1402 shows details of an LOC and detection optics. The illustrated LOC is in a disc format. Disc rotation is around the depicted axis vertically in the plane of figure. Left to right in the figure is radially on the disc. In some examples, the irradiation wavelength λ=405 nm, the lens has a numerical aperture (NA) of 0.85, and the focused spot size is 0.39 μm ($1/e^2$). The illustrated reflective grating is arranged over a polymer substrate and has lands and grooves at a pitch P (groove-to-groove or land-to-land) of 500 nm and a groove depth D of 38 nm. Targets are illustrated as hatched ovals, and can include, e.g., Micro vesicles in a medium, such as blood plasma.

In some examples, resultant light is detected by one or more OEIC(s), PMT(s), or other optical detectors. In some examples, e.g., as described herein with reference to FIGS. 19-21, a PMT can be configured to detect fluorescent emissions from target(s), and the output of the PMT can be provided to a discriminator or photon counter.

The illustrated example includes a focused scanning laser spot on reflective grating and single photon detection. However, in some examples, a substantially flat reflective surface is used instead of the illustrated land/groove (L/G) structure.

Figure 15:
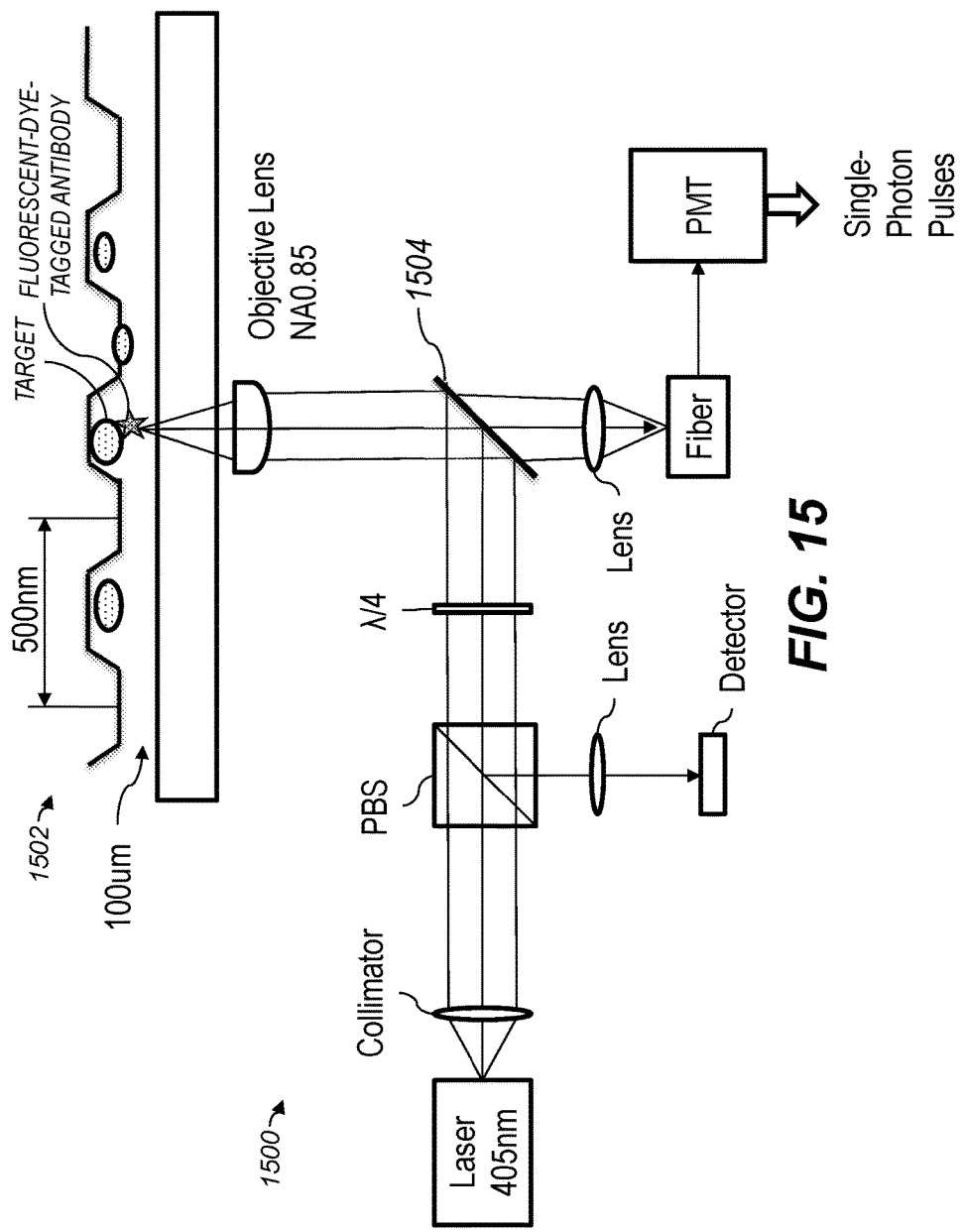
FIG. 15 shows components of an example measurement system, including sample carrier and optical detection components.

FIG. 15 shows example detection optics 1500, e.g., for microvesicles, and an example of a sample carrier 1502. In the illustrated example, a laser (e.g., $\lambda$=405 nm) illuminates a reflective grating (e.g., of an LOC) through an objective lens. As shown, a target (e.g., a microvesicle or other microparticle, depicted as an oval) is arranged over the reflective grating. An antibody (depicted as a star) is bound to the target. In this example, the antibody is tagged with a fluorescent dye. When the illumination strikes the dye, the die fluoresces. Additionally, the reflective grating and the target interact to modulate, scatter, reflect, or refract some of the incident light.

In the illustrated example, reflected light from the grating at the incident wavelength is passed through a pellicle, polarization, or other beamsplitter to a detector array (e.g., split photodetector 1102 to produce high-frequency (HF), radial push-pull (RPP), tangential push-pull (TPP), or focus error signals. Light not at the incident wavelength, e.g., emitted by fluorescent dyes on antibodies bound to targets in the sample, passes through mirror 1504 and is collected by a lens and coupled into an optical fiber. Mirror 1504, in some examples, is configured to reflect light (e.g., substantially all light) at the incident wavelength (here, 405 nm) and to transmit light (e.g., substantially all light) at wavelengths longer than the incident wavelength. In order to collect the fluorescent light to the fiber, a collimator lens can be used, e.g., a collimating aspherical lens similar to that used to collimate laser light. In some examples, the 405 nm irradiation spot is a diffraction limited spot. In some examples, aberration can be present in the fluorescent-collection optics and the fluorescent light can couple to the fiber having a core diameter, e.g., ~0.1 mm–~0.6 mm in diameter. The fiber carries the light to a photomultiplier tube (PMT) or other optical detector. In some examples, the fluorescence signal is detected by detection of single photons without averaging. In some examples, detected photons are averaged with an FWHM time constant $\tau$=DFWHM/v. DFWHM is the diameter, e.g., in meters or microns, at FWHM. In some examples, high-NA optics are used to improve collection efficiency. In some examples, optics having low autofluorescence are used to reduce noise photons. Examples herein can provide high-speed single photon detection with low dark counts.

In some examples, anti-body reagent(s) or marker(s) are applied to specific micro vesicles. Then, fluorescence is detected from coupled micro vesicles (MVs). Compared to a large live cell (e.g., 10 μm diameter), MVs have a much smaller particle surface and volume. Assuming a sphere shape, example ratios are given in Table 5.

TABLE 5

| Particle Diameter | Diameter Ratio | Surface Ratio | Volume Ratio |
|---|---|---|---|
| 10 μm | 1.0 | 1.0 | 1.0 |
| 1 μm | 1/10 | 1/100 | 1/1,000 |
| 0.1 μm | 1/100 | 1/10,000 | 1/1,000,000 |
| 0.01 μm | 1/1,000 | 1/1,000,000 | 1/1,000,000,000 |

For example, if 1,000,000 conjugated anti-bodies bind on a 10 μm size, 0.1 μm-size cell, 1,000,000×1/10,000=100 dye molecules bind to a 0.1 μm microvesicle, in a nonlimiting example.

Under irradiation, e.g., laser light, dye molecules emit photon(s) by electron excitation and decay. Photon ratio, QE (quantum efficiency), is emitted photons divided by excited photons. Photon energy is E=1.24/$\lambda$ (eV). For some dye molecules, once the molecule is excited and the photon emitted, the dye molecule is quenched (photo bleaching). Therefore, some examples provide exposure to fresh dye molecules over time to improve system response. Some examples do this using a flying spot, e.g., by scanning irradiation across a sample containing dyed antibodies conjugated to targets. Some examples include rotating a substrate holding the samples to move samples and irradiation with respect to each other. Some examples including moving a substrate linearly. Some examples include moving targets, e.g., using a flow of carrier fluid. In some examples, in order to excite a target (e.g., a microvesicle or other micro particle) with sufficient intensity and without overlapping other nearby targets, a focused small laser spot is used. In some examples, a flow cell is used. Moving an irradiation spot with respect to a target (e.g., with respect to a sample or reflective surface bearing the sample) can permit reducing the effect of photo-bleaching, improving detection effectiveness.

Figure 16:
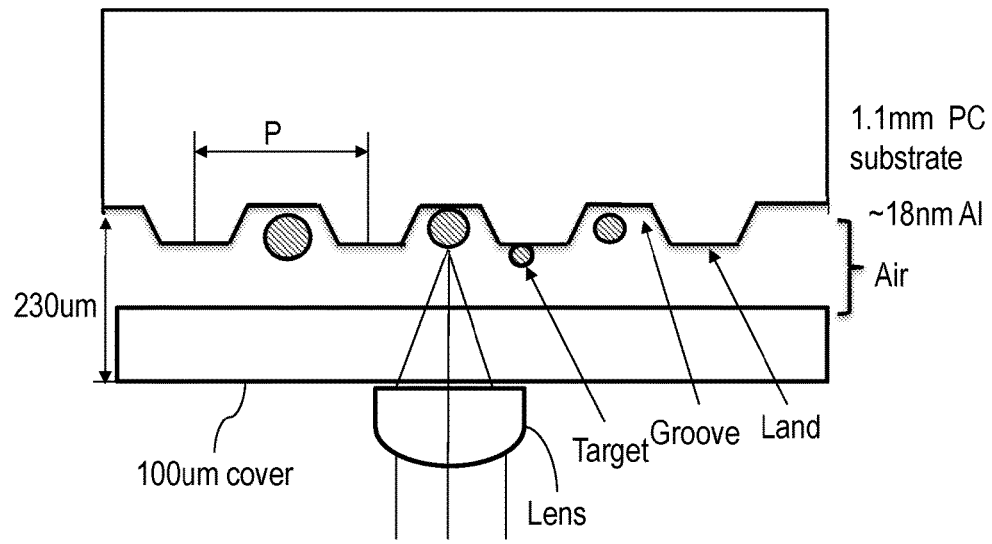
FIG. 16 shows a components of an example measurement system, including sample carrier and optical detection components.

FIG. 16 shows another example configuration of detection of microparticles on a reflective grating. The illustrated configuration includes a 1.1 mm-thick polycarbonate (PC) substrate overcoated with an ~18 nm-thick Al reflective layer (or ~20 nm, ~100 nm, >100 nm, etc.). A 100 μm-thick cover, e.g., also PC, is spaced apart from the substrate to form a channel or other sample chamber. The channel can be filled with air or another fluid, e.g., a gas or liquid. The base of the grooves is 230 μm from the far side of the cover in this nonlimiting example. The groove pitch P can be, e.g., 500 nm, and the grooves can be 38 nm deep.

Figure 17:
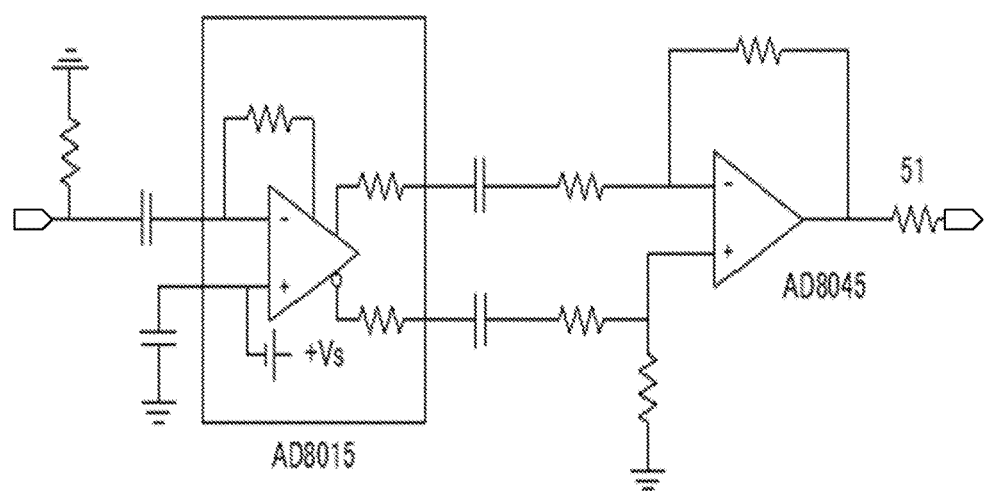
FIG. 17 is a circuit diagram of components of an example amplifier.

FIG. 17 shows an example transimpedance amplifier useful with various examples. The illustrated example amplifier has a 70 MHz bandwidth (BW) and can output analog signals to an ND converter input. In some examples, tested micro-photomultiplier tubes (pPMTs) with an example I-V amp achieved 100 MHz BW with 6 ns pulse width.

In some examples, a gating signal is produced based at least on the HF and TPP signals. Further details are discussed herein with reference to FIGS. 19-21. In some examples, a gating function is used to distinguish signal photons from thermal-noise photons or other photons produced by substances other than target dyes or other chromophores capable of associate with targets.

Various aspects, e.g., some aspects described herein with reference to FIG. 1-7, 10-16, 18, 19, 23, 24, or 26-28, include at least some of a reflective phase grating arranged in or adjacent to a microfluidic channel, a sample-delivery system, an irradiation system, and a detection system. Using a reflective grating provides effective optics and doubles phase detection compared to some prior schemes. Using a reflective grating also permits using low-cost manufacturing techniques developed for CD, DVD, and BLU-RAY discs (providing, e.g., 3 s per disc manufacturing time). The irradiation system can include one or more lenses or scanners to provide a focused scanning spot, e.g., a focused scanning laser spot. The detection system can include on or more photomultiplier tubes (PMTs) or other optical detectors. PMTs can be used, e.g., to detect fluorescence from targets or from dyes (e.g., containing fluorochromes) in, on, or associated with targets. The sample-delivery system can include a filter, e.g., to separate red blood cells from plasma so that targets in the plasma, e.g., microvesicles, can be measured apart from the red blood cells.

In various aspects, targets such as nanoparticles are detected as HF and PP signal perturbations caused by optical path differences such as different optical path length. In various aspects, the detected HF pulse width and tangential PP signal modulation are used to determine tangential particle size. In various aspects, radial PP signal modulation is used to determine radial particle size. Various aspects use radial PP together with HF or tangential PP (or both) to provide 2D data of targets.

Various aspects include a substrate including a microfluidic channel on, over, or adjacent to a reflective phase grating. The microfluidic channel can have a height (away from the grating), e.g., of <5 µm. These aspects can be embodied in, e.g., LOC structures. LOCs can include rigid, semi-rigid, or flexible substrates.

Various aspects, e.g., of LOCs, include disposable chips having sample-processing structures such as cell-separation structures, staining structures, filtering structures, measurement structures, and waste-retention structures. Such aspects can be used, e.g., in clinical applications. For example, LOCs can be used to perform high-volume analysis of samples from many patients in a hospital, or many customers of an analysis lab.

Various aspects include an optical assembly including a tracking system for focusing and tracking of a focused spot such as a laser spot, e.g., a focused laser spot, on a reflective grating. The tracking system can operate in rotation, e.g., for disc-format LOCs, or in traverse (e.g., X-Y axis), e.g., for slide-glass-shaped LOCs.

In some examples, microvesicles or other targets adhere to lands or grooves of a disc or LOC, e.g., due to electric field interactions, van der Waal's forces, surface tension and wetting of the surface of the disc, or other microscale interactions. Reflective surfaces, e.g., reflective gratings, can have surface materials, finishes, electrical or magnetic characteristics, or other properties configured to retain a sample, e.g., a fluidic or non-fluidic sample, at least partly in a detection zone such as that illustrated in FIG. 1.

Various aspects include acts to enhance refractive index difference between particles and medium. For example, a sugar solution can be selected to have a different refractive index than the targets of interest. In some examples, air is used as a medium so n≈1. In some examples, a polymer medium is used and the wavelength of light is selected to achieve a desired $n_\lambda$ of the polymer. In some examples, water or another aqueous medium is used and solutes are added to adjust refractive index n or dielectric constant k of the medium. For example, a 10% glucose solution can have a refractive index of 1.3477, a 20% glucose solution 1.3635, or a 60% glucose solution 1.4394. In some examples, the refractive index of the medium can be varied and measurements can be taken at various medium n values, e.g., continuously or in discrete steps. A refractive index of the medium can be selected, e.g., from those tested, that provides a selected signal-to-noise ratio or other metric of measurement quality.

In some examples, statistics of the measured data are gathered to, e.g., extrapolate from measurements of fewer than all of the particles. For example, average particle size can be computed from measurements of a selected number of particles.

Various aspects include data acquisition and analysis software for detecting variations in the light reflected off a reflective phase grating.

Various aspects include structures or techniques for fluorochrome staining of microvesicles or other targets. These aspects can be used to identify the origins, compositions, or identities of particles, or to distinguish particles from background noise such as electrical noise. Electrical noise can include, e.g., shot noise in the photodetectors measuring light reflected by the phase grating.

Various aspects include scanning of phase gratings, focused laser spots, or both. Scanning can be performed by mechanical scanning devices such as disc rotation systems or X-Y stages, or by optical scanning devices such as galvanometer motors ("galvos") or beam deflectors.

Various aspects include one or more of the following properties: (a) Detection optics: $\lambda$=405 nm, NA=0.85, cover thickness=0.1 mm, focused spot size=0.39 µm(1/e2), p>240 nm, or any combination of those; (b) Reflective phase grating groove depth of $\lambda$/8n; (c) Reflective-grating pitch p>$\lambda$/2NA; (d) A disc structure having a spiral groove in which successive turns are separated by the pitch p; (e) p=1.6 µm, p=0.74 µm, or p=0.32 µm; (f) Phase grating depth ~40 nm and pitch p=500 nm; (g) Phase-grating land-groove aspect ratio is 50:50. Other ranges can be used, e.g., 60:40 or 40:60; (h) A disc structure in which the reflective phase grating is arranged around a center of the disc between about 38 mm from the center and about 42 mm from the center; (i) A detection region with no grooves, e.g., a mirror or substantially flat metal surface of a disc or other LOC; (j) Servo bandwidth <50 kHz and particle signal bandwidth >100 kHz; (k) Data acquisition has sufficient bandwidth (BW) and resolution. E.g., at 1.0 m/s scanning velocity, a 10 nm particle can be detected as a 10 ns-wide pulse. Measurement hardware having a bandwidth of 200 MHz (5 ns) can be used in this example. In some examples, signal rise time can be computed as 0.35/BW. Signals with a 5 ns rise time can therefore be measured with hardware having at least 70 MHz BW; (l) Detecting fluorescence of micro particles with a conjugated anti-body; (m) Detecting fluorescence of microparticles stained with a dye. For example, proteins can be stained with FITC, lipids with Nile red, or DNA with Hoechst 33342. Other dyes can be selected for use depending on the excitation wavelength; (n) Excitation by a focused flying laser spot with smaller than 2 µm FWHM; (o) Detecting single photon pulses without averaging, e.g., less than 20 ns width; (p) Detecting photon pulses with time constant ~$\tau$=DFWHM/v; (q) Distinguishing signal & noise photons by gating with HF/Push-Pull signals from particles, e.g., HF and TPP; (r) Investigating micro particle fluorescence by single photon spectroscopy; (s) Measuring microvesicles; (t) Detecting fluorescence and providing imaging for micro and nano particles.

In some examples, one focusing point is sufficient since the number of microvesicles is relatively high. In other examples, multiple focusing points are used (e.g., in-groove and on-land).

In view of the foregoing, various aspects provide effective detection or size measurement of small particles. A technical effect of various aspects is to measure physical properties of a sample, e.g., a sample of blood or another bodily fluid.

Figure 18:
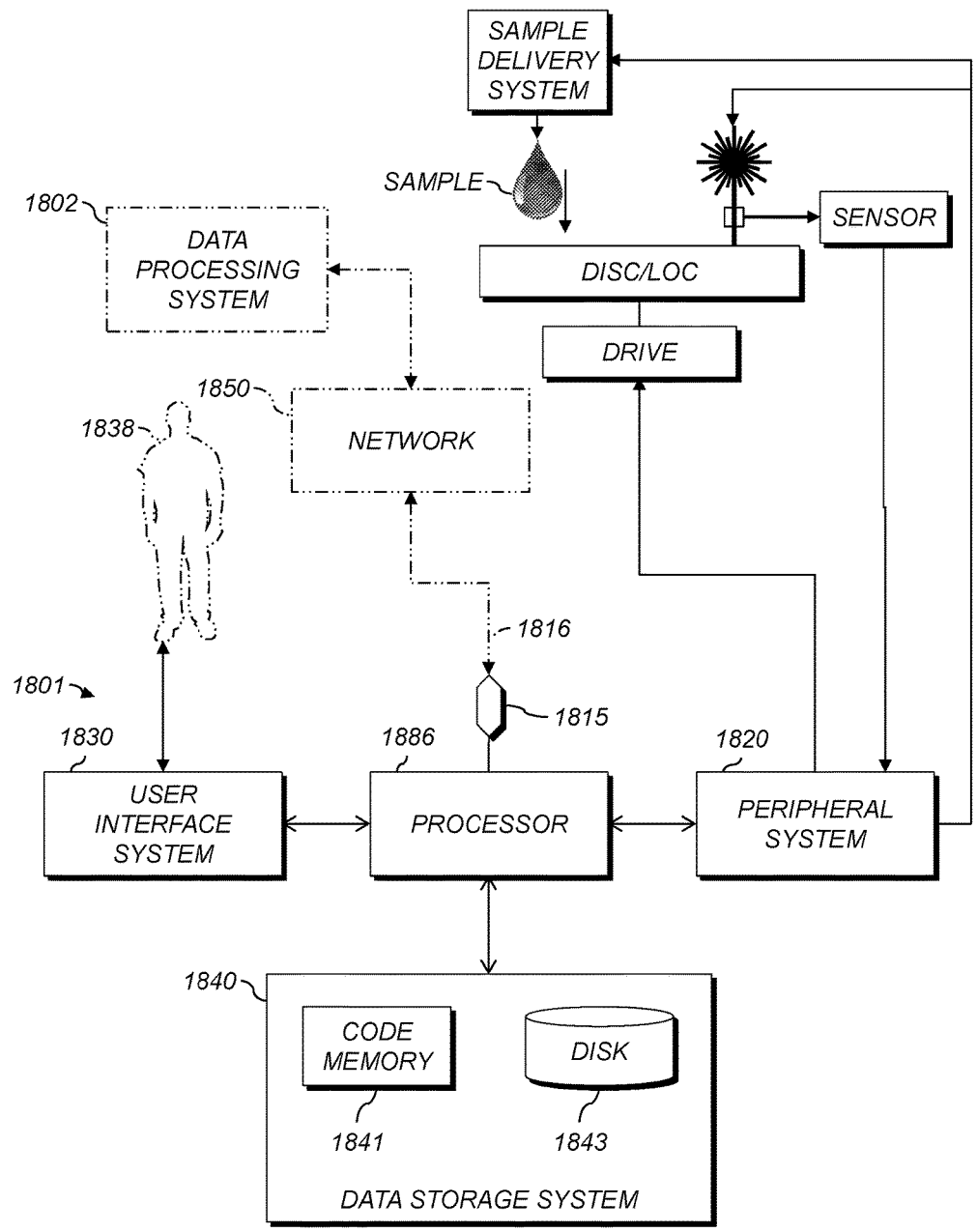
FIG. 18 is a block diagram showing components of an example measurement system, including data-processing components useful with various examples.

FIG. 18 is a high-level diagram showing the components of an example data-processing system 1801 for analyzing data and performing other analyses described herein, and related components. The system 1801 includes a processor 1886, a peripheral system 1820, a user interface system 1830, and a data storage system 1840. The peripheral system 1820, the user interface system 1830 and the data storage system 1840 are communicatively connected to the processor 1886. Processor 1886 can be communicatively connected to network 1850 (shown in phantom), e.g., the Internet or a leased line, as discussed below. At least one of the systems shown in FIG. 12-15, 17, or 19 can include at least one of systems 1886, 1820, 1830, 1840, and can connect to one or more network(s) 1850. Processor 1886, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1886 can implement processes of various aspects described herein. Processor 1886 and related components can, e.g., carry out processes for receiving a sample on a substrate having a reflective phase grating thereon or thereover, irradiating the sample with a focused spot of light while traversing over the substrate, detecting variations in reflected light, and determining properties of a target (e.g., presence, size, orientation) using the detected variations. Processor 1886 and related components can, e.g., carry out processes for making discs or LOCs by controlling mastering equipment to make stampers, mold discs or LOCs using stampers, sputter discs or other LOCs, or apply cover materials to discs or LOCs.

Processor 1886 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as peripheral system 1820, user interface system 1830, and data storage system 1840 are shown separately from the processor 1886 but can be stored completely or partially within the processor 1886.

The peripheral system 1820 can include or be communicatively connected with one or more devices configured or otherwise adapted to provide digital content records to the processor 1886 or to take action in response to processor 1886. For example, the peripheral system 1820 can include digital still cameras, digital video cameras, cellular phones, or other data processors. The processor 1886, upon receipt of digital content records from a device in the peripheral system 1820, can store such digital content records in the data storage system 1840.

In the example shown, peripheral system 1820 is connected to a drive, a sensor, a laser, and a sample-delivery system. The drive spins the disc (in other configurations, the drive can scan a laser across a stationary LOC), e.g., as done to spin BLU-RAY discs. The sample-delivery system applies to the disc or other LOC fluid samples to be measured for the presence or properties of targets. For example, the sample-delivery system can include an automated pipette or other metering system for applying a selected amount of sample. The laser irradiates the disc or other LOC and the sensor measures reflected light (illustrated as coming from a beamsplitter, though other configurations can be used, e.g., a laser at an angle to the substrate other than normal). Processor 1886 and peripheral system 1820 coordinate these components to measure the samples and target(s) therein. Other examples of components that can be operated by processor 1886 are shown in FIG. 12-15, 17, or 19. Various examples of LOCs that can be used with components shown in FIG. 18 are shown in FIGS. 1-11, 16, and 23.

In some examples, processor 1886 can provide control signals, e.g., as discussed above with reference to FIG. 14, to adjust a focal position of the spot of light with respect to the reflective surface. For example, processor 1886 can provide the control signals to rasterize the spot of light in three dimensions, to repeatedly scan the spot of light substantially normal to at least a portion of the reflective surface (e.g., normal N in FIG. 1), or to focus the spot of light, e.g., to detect particles within a groove (e.g., longer focal distance) or to detect particles on a land (e.g., shorter focal length).

The user interface system 1830 can convey information in either direction, or in both directions, between a user 1838 (or other entity) and the processor 1886 or other components of system 1801. The user interface system 1830 can include a mouse, a keyboard, another computer (connected, e.g., via a network or a null-modem cable), or any device or combination of devices from which data is input to the processor 1886. The user interface system 1830 also can include a display device, a processor-accessible memory, or any device or combination of devices to which data is output by the processor 1886. The user interface system 1830 and the data storage system 1840 can share a processor-accessible memory.

In various aspects, processor 1886 includes or is connected to communication interface 1815 that is coupled via network link 1816 (shown in phantom) to network 1850. For example, communication interface 1815 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WIFI or GSM. Communication interface 1815 sends and receives electrical, electromagnetic, or optical signals that carry digital or analog data streams representing various types of information across network link 1816 to network 1850. Network link 1816 can be connected to network 1850 via a switch, gateway, hub, router, or other networking device.

In various aspects, system 1801 can communicate, e.g., via network 1850, with a data processing system 1802, which can include the same types of components as system 1801 but is not required to be identical thereto. Systems 1801, 1802 are communicatively connected via the network 1850. Each system 1801, 1802 executes computer program instructions to, e.g., carry out measurements as described herein.

Processor 1886 can send messages and receive data, including program code, through network 1850, network link 1816 and communication interface 1815. For example, a server can store requested code for an application program (e.g., a JAVA applet) on a tangible non-volatile computer-readable storage medium to which it is connected. The server can retrieve the code from the medium and transmit it through network 1850 to communication interface 1815. The received code can be executed by processor 1886 as it is received, or stored in data storage system 1840 for later execution.

Data storage system 1840 can include or be communicatively connected with one or more processor-accessible memories configured or otherwise adapted to store information. The memories can be, e.g., within a chassis or as parts of a distributed system. The phrase "processor-accessible memory" is intended to include any data storage device to or from which processor 1886 can transfer data (using appropriate components of peripheral system 1820), whether volatile or nonvolatile; removable or fixed; electronic, magnetic, optical, chemical, mechanical, or otherwise. Example processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1840 can be a tangible non-transitory computer-readable storage medium, i.e., a non-transitory device or article of manufacture that participates in storing instructions that can be provided to processor 1886 for execution.

In an example, data storage system 1840 includes code memory 1841, e.g., a RAM, and disk 1843, e.g., a tangible computer-readable rotational storage device or medium such as a hard drive. Computer program instructions are read into code memory 1841 from disk 1843. Processor 1886 then executes one or more sequences of the computer program instructions loaded into code memory 1841, as a result performing process steps described herein. In this way, processor 1886 carries out a computer implemented process. For example, steps of methods described herein, blocks of the flowchart illustrations (e.g., FIGS. 24-28) or block diagrams herein, and combinations of those, can be implemented by computer program instructions. Code memory 1841 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code ("program code") stored on a computer readable medium, e.g., a tangible non-transitory computer storage medium or a communication medium. A computer storage medium can include tangible storage units such as volatile memory, nonvolatile memory, or other persistent or auxiliary computer storage media, removable and non-removable computer storage media implemented in any method or technology for storage of information such as computer-readable instructions, data structures, program modules, or other data. A computer storage medium can be manufactured as is conventional for such articles, e.g., by pressing a CD-ROM or electronically writing data into a Flash memory. In contrast to computer storage media, communication media may embody computer-readable instructions, data structures, program modules, or other data in a modulated data signal, such as a carrier wave or other transmission mechanism. As defined herein, computer storage media do not include communication media. That is, computer storage media do not include communications media consisting solely of a modulated data signal, a carrier wave, or a propagated signal, per se.

The program code includes computer program instructions that can be loaded into processor 1886 (and possibly also other processors), and that, when loaded into processor 1886, cause functions, acts, or operational steps of various aspects herein to be performed by processor 1886 (or other processor). Computer program code for carrying out operations for various aspects described herein may be written in any combination of one or more programming language(s), and can be loaded from disk 1843 into code memory 1841 for execution. The program code may execute, e.g., entirely on processor 1886, partly on processor 1886 and partly on a remote computer connected to network 1850, or entirely on the remote computer.

Figure 19:
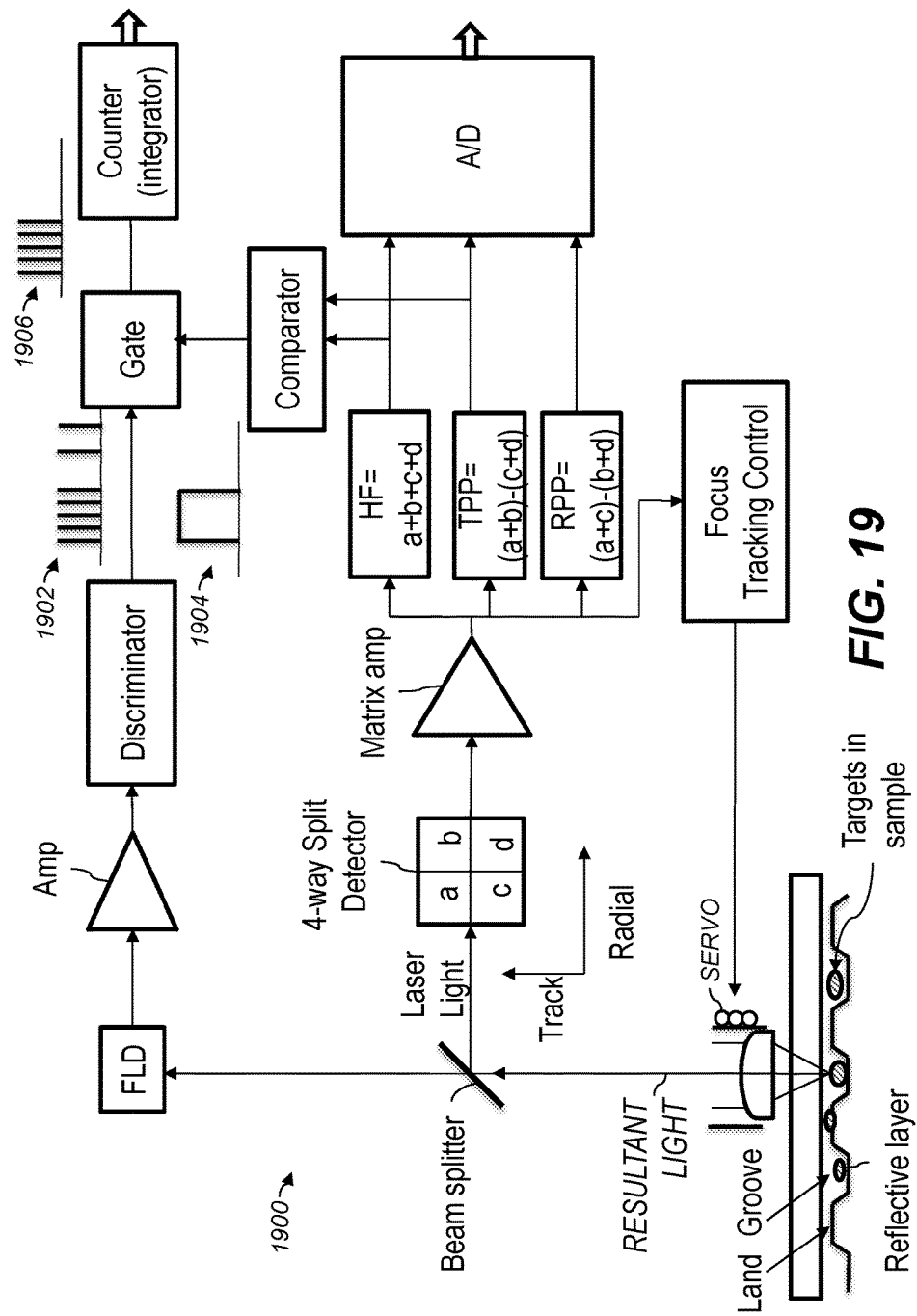
FIG. 19 shows components of an example measurement system, including gating components.

FIG. 19 shows a block diagram of an example measurement system 1900 incorporating gating logic. Resultant light is divided between the split photodetector (light substantially at the incident A) and the fluorescence detector (other than A), e.g., as described above with reference to FIG. 12. Tracking signals from the split photodetector are used by the focus/tracking control block to determine drive for a servo to maintain tracking or focus.

HF and TPP signals are produced and provided to a comparator. The comparator provides a gating function, e.g., by thresholding or detecting edges of, e.g., the HF or TPP signals from the split photodiode. Various examples of comparators are discussed below with reference to FIG. 20. The HF, TPP, and RPP signals can also be digitized by an ND converter and provided, e.g., for particle analysis.

A signal from a fluorescence detector (FLD), e.g., a pPMT, can be passed through a discriminator. The discriminator can remove noise, e.g., thermal noise. In some examples, the discriminator removes pulses having a pulse height (e.g., measured in volts) smaller in magnitude than a selected lower level of discrimination (LLD). In some examples, the discriminator removes pulses having a pulse height larger in magnitude than a selected upper level of discrimination (ULD). The resulting pulses 1902 are gated by the gating function ("Gate"), e.g., by passing pulses only when the gating function 1904 has a high logic value or other gate-open value. The gated pulses 1906 are counted. The counts of pulses can then be provided for fluorescence analysis. In some examples (omitted for brevity), gating can be additionally or alternatively based in RPP signals.

Figure 20:
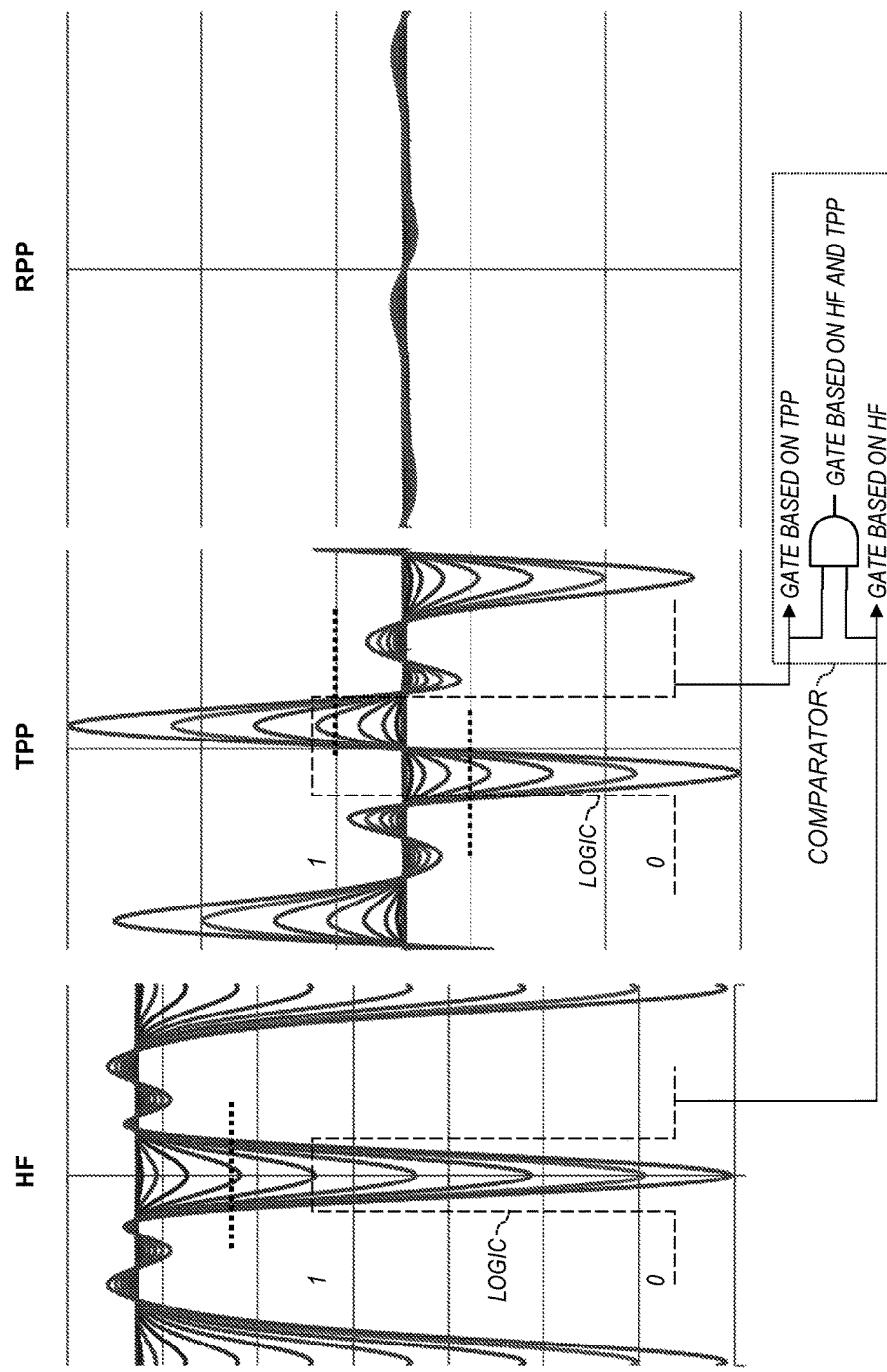
FIG. 20 shows simulated tracking signals and example gating components of an example measurement system.

FIG. 20 shows simulated HF, TPP and RPP signals. In the example plots, a particle as centered at zero on the X-axis. Units on both axes or arbitrary. The axes can be, e.g., microns on the X-axis and volts on the Y-axis. The curves show respective, different particle sizes from 10 nm-100 nm.

On the left-hand, HF plot, the dotted line shows a threshold. In some examples, a gating signal corresponding to the HF signal has a true logic value (e.g., a 1 value) when the HF signal is below the threshold, as represented by the dashed line. In other examples, the gating signal corresponding to the HF signal has a true logic value when the HF signal is above the threshold, within a specified range, or outside a specified range. In an example, the gate is open (true logic level) during the 240 ns FWHM of a laser pulse.

On the center, TPP plot, the TPP signal has a negative excursion when beginning to cross the particle and a positive excursion when leaving the particle. The dotted lines show thresholds for the excursions. In the illustrated example, the logic signal (dashed) corresponding to the TPP signal has a true logic value between the low-going crossing of the threshold in the negative excursion and the low-going crossing of the threshold in the positive excursion.

In some examples, the gate is open (photons are counted) when the HF logic signal has a true logic value, when the TPP logic signal has a true logic value, or when both the HF and TPP logic signals have true logic values. These examples are illustrated in the box labeled "Comparator."

In some examples, the size of a particle is determined from the height and width of the HF pulse, e.g., by measuring levels of the HF pulse, ramp rates of the HF pulse, or FWHM of the HF pulse. For example, D-FWHM or the duration of the true logic level on the HF logic signal can indicate particle size. In some examples, the size of a particle is determined from the duration of the true logic level on the TPP logic signal, or from the heights or widths of the excursions on the TPP signal. In some examples, the lateral position of the particle in the groove or on the land is determined using the pulse height or ripple of the RPP signal.

Figure 21:
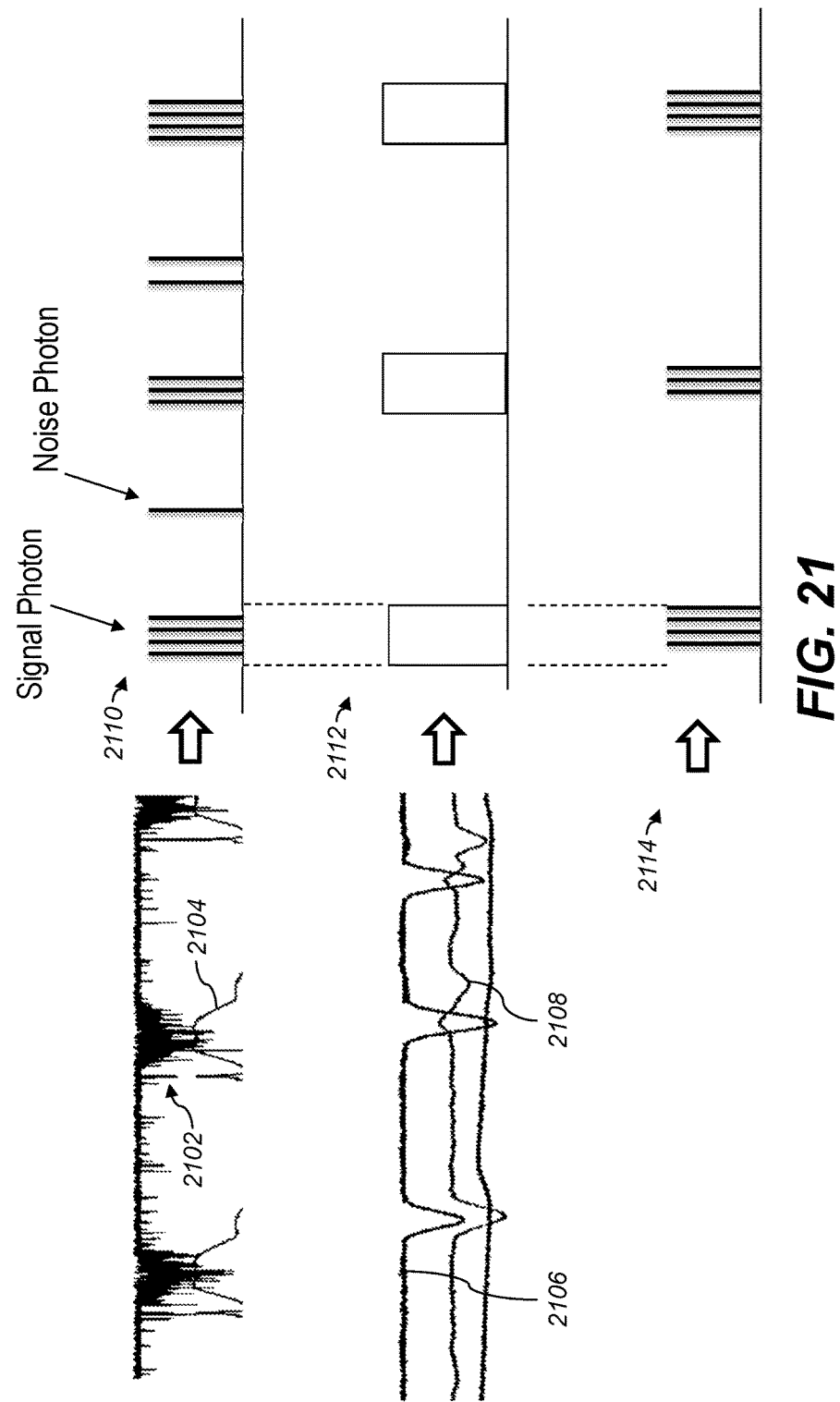
FIG. 21 shows measured and representative example tracking signals, and representative example gating signals.

FIG. 21 shows examples of photon pulses and gating. Curve 2102 shows measured photon pulses. Curve 2104 (shown only partially) shows comparator outputs. Curve 2106 shows a measured HF signal. Curve 2108 shows a measured TPP signal. Plot 2110 shows simulated example photon pulses. Plot 2112 shows simulated example gating signals. Plot 2114 shows pulses resulting from the gating of plot 2110 with the gating signal of plot 2112. As shown in plot 2114, gating can permit discarding noise-photon pulses and retaining signal-photon pulses.

Figure 22:
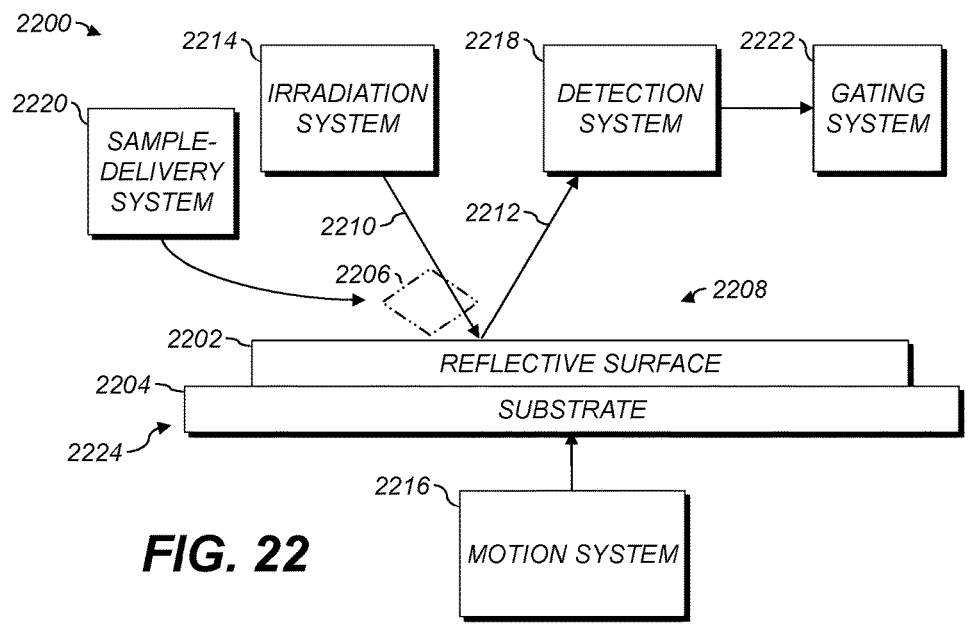
FIG. 22 is a schematic of an example target-measurement system.

FIG. 22 shows an example target-measurement system 2200. System 2200 can represent systems described herein with reference to FIG. 1, 6, or 11-20. A reflective surface 2202, e.g., over a substrate 2204 of a sample carrier such as an LOC, is configured to retain a target 2206 (shown in phantom), e.g., a microscale target, in a detection region 2208 and to reflect at least part of a focused spot 2210 of light to provide resultant light 2212, e.g., reflected light, diffracted light, or other resultant light. An irradiation system 2214 is configured to irradiate at least part of the detection region 2208 with the focused spot 2210. The illustrated angle of incidence of focused spot 2210 is for clarity of explanation and is not limiting. A motion system 2216 is configured to cause motion of the focused spot 2210 relative to the reflective surface 2202. Although illustrated as causing motion of substrate 2204, this is not limiting. Motion system 2216 can additionally or alternatively cause motion of focused spot 2210 with respect to reflective surface 2202, a sample thereon, or target 2206. Examples are discussed above, e.g., with reference to FIG. 1, 7-16, 18, or 19.

A detection system 2218 is configured to detect the resultant light 2212, e.g., as described herein with reference to FIGS. 12-19. Examples of LOCs useful with target-measurement system 2200 are described herein with reference to FIG. 1-11, 14-16, or 23. Examples of irradiation system 2214, motion system 2216, or detection system 2218 are described herein with reference to FIGS. 11-20.

In some examples, a sample-delivery system 2220 is configured to apply a sample comprising the target 2206 to at least a portion of the detection region. Examples of sample-delivery systems 2220 and other components useful with various examples of system 2200 are described herein with reference to FIG. 1, 6-9, or 18. In some examples, a gating system 2222 is configured to provide a particle signal associated with a temporal overlap between at least one of the plurality of detection signals and the second detection signal. Examples of gating system 2222 are described herein with reference to FIGS. 19-21.

In some examples, a target holder 2224 can be configured to retain target 2206 in detection region 2208. Target holder 2224 can comprise reflective surface 2202 configured to reflect at least part of the focused spot 2210 of light to provide the resultant light 2212. In some examples, target holder 2224 can comprise one or more LOCs as described herein, e.g., with reference to FIGS. 1-11. In some examples, reflective surface 2202 can be separate from, e.g., spaced apart from, target holder 2224. For example, target holder 2224 can include transparent structures to retain target 2206, e.g., in a fluidic sample, over a mirror or reflective grating (reflective surface 2202), when viewed along an irradiation direction of the spot 2210 of light.

System 2200 can be an example of a target-measurement assembly, as can other systems described herein, e.g., with reference to FIG. 1, 13-16, 18, or 19. As used herein, the term "assembly" does not require that the components of the assembly be physically mounted to each other. An assembly, e.g., system 2200, can include multiple components configured to interoperate. In some examples, an assembly can comprise an LOC and a measurement platform. The LOC can comprise reflective surface 2202 and substrate 2204. The measurement platform can comprise at least some of irradiation system 2214, motion system 2216, detection system 2218, sample-delivery system 2220, or gating system 2222. The measurement platform can be configured to receive the LOC and perform operations, e.g., described herein with reference to FIGS. 24-28.

Figure 23:
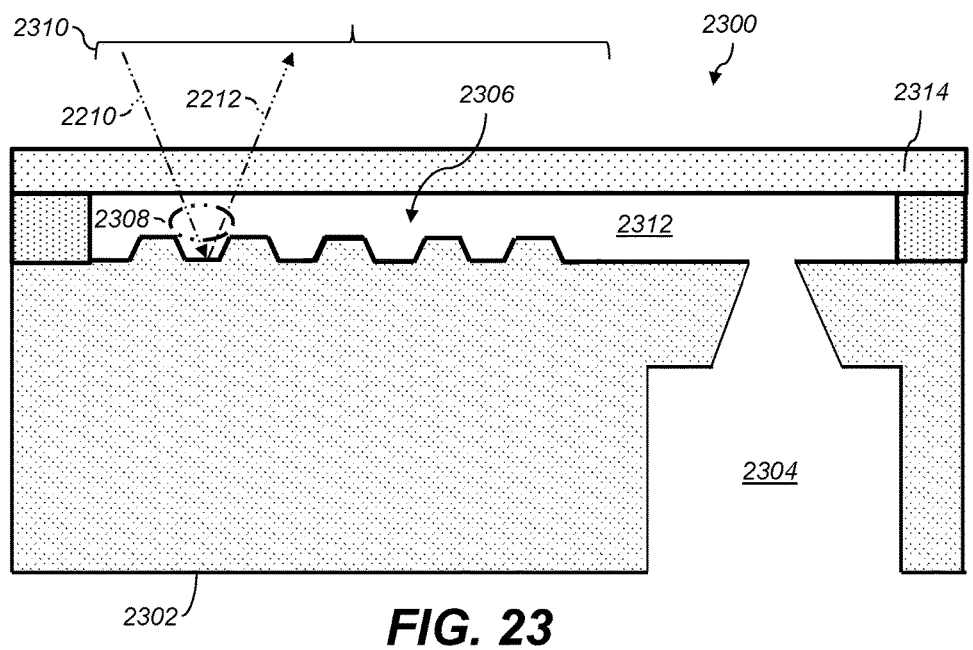
FIG. 23 is a schematic elevational cross-section of an example LOC.

FIG. 23 shows an example device 2300, e.g., a sample carrier such as an LOC. Device 2300 can represent devices described herein with reference to FIG. 1-11, 14-16, or 18-20. Device 2300 can additionally or alternatively represent target holder 2224, FIG. 22. Device 2300 includes a substrate 2302 and a sample inlet 2304 arranged on, in, or over the substrate 2302. A reflective grating 2306 or other reflective surface is arranged on, in, or over the substrate 2302. The reflective grating 2306 is configured to retain a fluidic sample 2308 (shown in phantom) in a detection region 2310, e.g., in or of a fluidic channel 2312. The detection region 2310 is fluidically connected to the sample inlet 2304. The detection region 2310 is operatively arranged with respect to the reflective grating 2306 so that at least some light passing through the detection region 2310 towards the reflective grating 2306 (e.g., light of the focused spot 2210, shown in phantom) also passes through the detection region 2310 after reflecting or diffracting off the reflective grating 2306 (e.g., resultant light 2212, shown in phantom). For example, the detection region 2310 can be arranged between the reflective grating 2306 and an irradiation system 2214, FIG. 22. In some examples, device 2300 can include a cover 2314, e.g., as described herein with reference to FIG. 1 or 9; a reservoir, e.g., as FIG. 8, at least one groove, e.g., as FIGS. 2-7, 10, or 11; a filter, e.g., as FIG. 1; or multiple sample inlets or vacuum ports, e.g., as FIG. 6.

Illustrative Processes and Further Illustrative Examples

Figure 24:
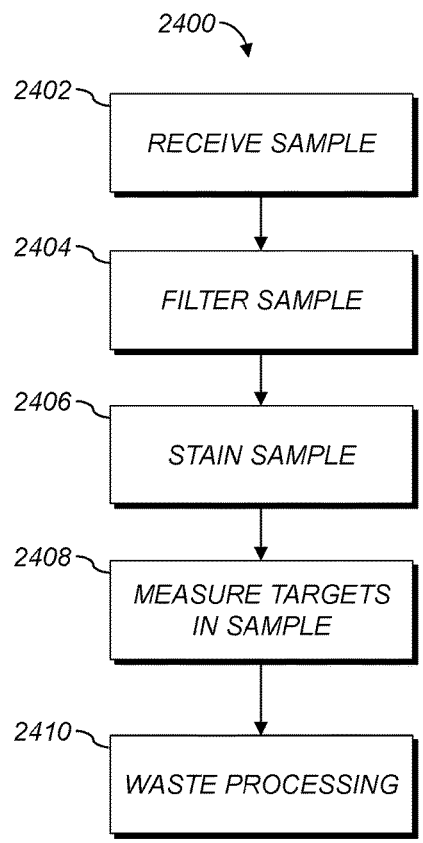
FIG. 24 is a flow diagram of an example process for analyzing a sample.

FIG. 24 shows a flowchart 2400 of example methods of measuring targets. Steps of FIG. 24 or other methods described herein, e.g., in FIGS. 25-28, can be performed in any order except when otherwise specified, or when data from an earlier step is used in a later step. For clarity of explanation, reference is herein made to various components shown in FIGS. 1-23 that can carry out or participate in the steps of the example method. It should be noted, however, that other components can be used; that is, example method(s) shown in FIGS. 24-28 are not limited to being carried out by the identified components. Methods described herein can be carried out by structures on an LOC, in conjunction with measurement systems described herein.

Methods herein can be used, e.g., with liquid biopsy samples of human patients, or with samples of semiconductor-fabrication chemicals.

At block 2402, a sample can be received, e.g., a whole-blood sample or chemical sample. The sample can be received on an LOC or other sample carrier, e.g., as described herein with reference to FIG. 1-10 or 23. In some examples, block 2402 can include receiving the sample having a refractive index different from the refractive index of targets in the sample. In some examples, the refractive indices of the sample and the targets differ by Δn. In some examples, |Δn| can be ~0.05, or ~0.1, or ~0.05-~0.1, or greater than ~0.1, or greater than ~0.2. Various examples can improve detection, as sensitivity is proportional to Δn×d in some examples. In some examples, targets have more than one refractive index, e.g., as discussed below with reference to microvesicles. Δn can be computed with reference to the refractive index of at least one of an exterior, a membrane, or an interior of a target, or with respect to an average refractive index of the target as a whole. The sample can be selected to have a refractive index different from any of these refractive indices by any of the Δn values above. In some examples, respective refractive indices of at least one of the substrate, the reflective layer, or the cover can be selected to differ from at least one of the respective refractive indices of at least one of a target, a component of a target, or a sample by any of the Δn values listed above.

At block 2404, filtering can be performed. For example, cells can be filtered out of a whole-blood sample, or contaminants can be filtered out of any sample. In some examples, an LOC can include a filter element operatively arranged to filter a provided sample to provide the fluidic sample, e.g., as shown in FIG. 1 or 7. The filter element can include a filter, e.g., an open structure such as an open-cell foam or a woven fabric or plastic mesh, a micropillar matrix such as shown in FIG. 7, or any combination of any of those.

At block 2406, staining can be performed. For example, a dye or antibody such as described herein with reference to FIG. 15 can be added to the sample. Examples are described herein with reference to FIGS. 7, 15, and 19.

At block 2408, measurement can be performed. For example, the sample can be irradiated and resultant light detected, e.g., as described herein with reference to FIG. 1 or 11-20.

At block 2410, at least some of the sample can be processed as waste. For example, at least some of the sample can be removed from the LOC by a vacuum or other pump, retained in a reservoir or absorbent material of the LOC, or otherwise treated for storage or disposal. Examples of vacuum ports, reservoirs, or other waste-processing structures or techniques are described herein with reference to FIGS. 6-8.

Figure 25:
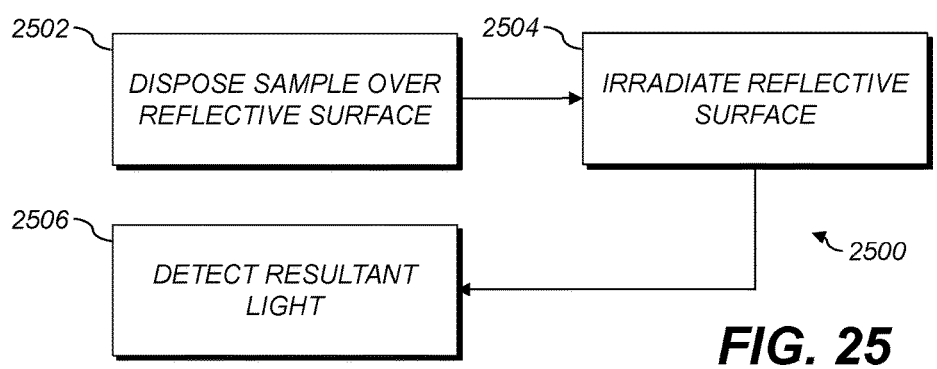
FIG. 25 is a flow diagram of an example process for detecting a target, e.g., in a sample.

FIG. 25 is a flow diagram of an example process 2500 for detecting a target. Block 2408 can include blocks 2504 or 2506.

At block 2502, a fluidic sample can be disposed over (e.g., on or above) a reflective surface. The reflective surface can include, e.g., a mirror or reflective grating. The fluidic sample can include a target, e.g., one or more microvesicles or microparticles. Block 2502 can include at least one of blocks 2402, 2404, or 2406, or can be performed between any one of blocks 2402, 2404, or 2406 and block 2408.

At block 2504, the reflective surface can be irradiated using a spot of light, e.g., a focused spot. In some examples, at least some of the sample over the reflective surface can be irradiated using the spot of light. Examples are discussed above, e.g., with reference to FIGS. 1 and 11-23.

At block 2506, resultant light from the reflective surface can be detected. In some examples, the resultant light can include light reflected or diffracted by the reflective surface, e.g., light diffracted by a reflective grating. Examples are discussed above, e.g., with reference to FIGS. 1 and 11-23.

Figure 26:
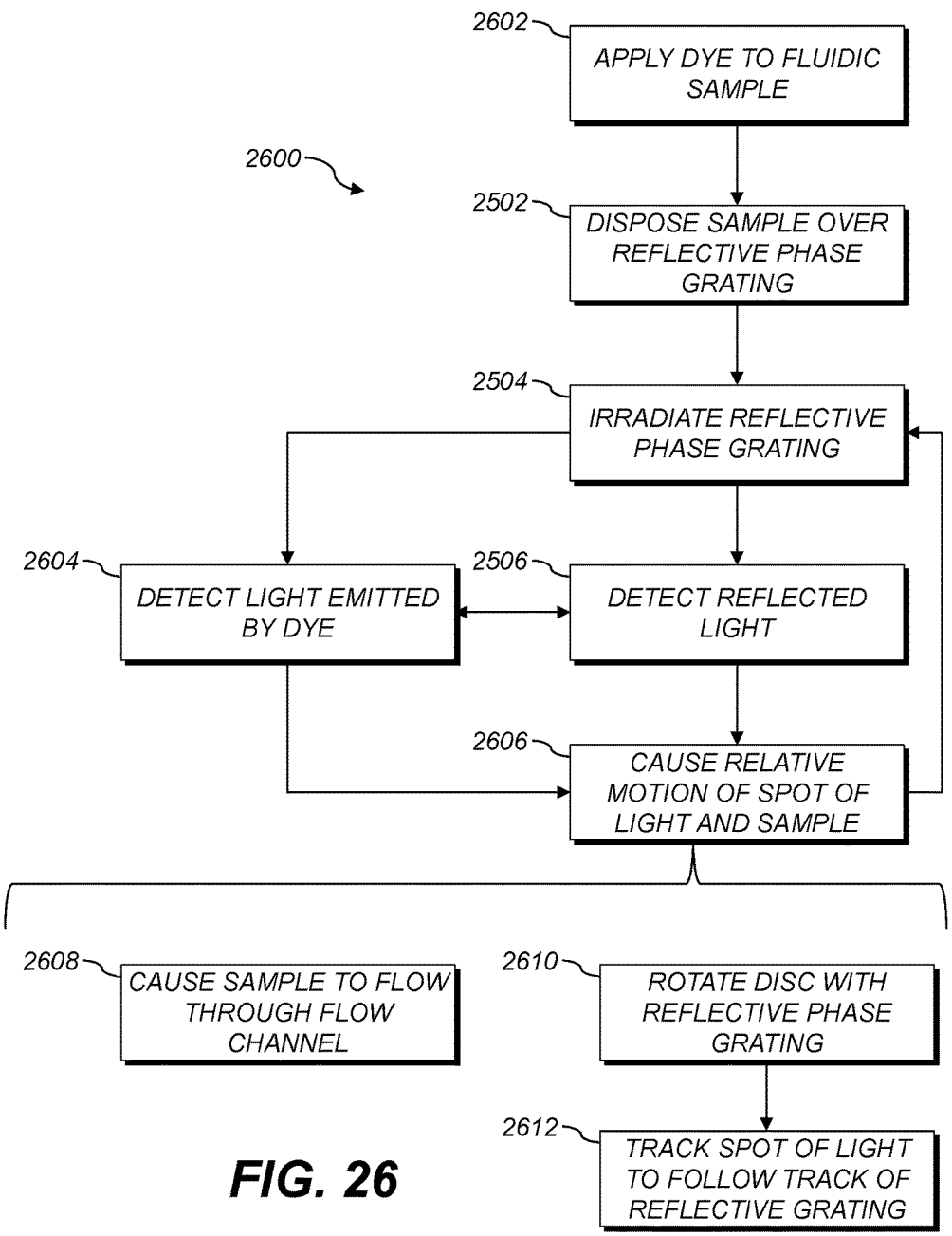
FIG. 26 is a flow diagram of an example process for detecting a target.

FIG. 26 is a flow diagram of an example process 2600 for detecting a target, e.g., in a sample. Some examples use blocks 2602 and 2604.

At block 2602, a dye can be applied to the fluidic sample before the disposing (block 2502). Examples are discussed above, e.g., with reference to block 2406.

At block 2604, light emitted by the dye can be detected. The light, e.g., fluorescence, can be emitted in response to the irradiating using the spot of light (block 2504). Examples are discussed above, e.g., with reference to FIG. 13-15 or 19.

At block 2606, relative motion can be caused of the spot of light and the fluidic sample. In some examples, block 2606 can include block 2608. In some examples, block 2606 can include blocks 2610 and 2612. Various examples of relative motion are described herein with reference to FIG. 1-16, 18, 19, 22, or 23, or Tables 2, 3, or 6.

At block 2608, in some examples, the fluidic sample can be pumped or otherwise caused to flow through a flow channel across the reflective surface. The spot can be caused to move with respect to the reflective surface at least partly across the flow channel. For example, the spot can be scanned, e.g., substantially perpendicular to the direction of flow, across the flow channel concurrently with the flowing of the sample. Various examples of flow are described herein with reference to FIG. 1, 6-10, 18, 22, or 23, or Tables 2, 3, or 6.

At block 2610, in some examples, a disc comprising the reflective surface can be rotated, e.g., as described herein with reference to at least FIG. 13. The disc can move with respect to the spot of light during the rotating. In some examples, block 2504 can include irradiating the reflective surface during the rotating.

At block 2612, in some examples, the spot of light can be caused to move to follow a track of the reflective surface, e.g., during the rotating. Examples are discussed above, e.g., with reference to FIGS. 2-4, 11, 14, and 19.

Figure 27:
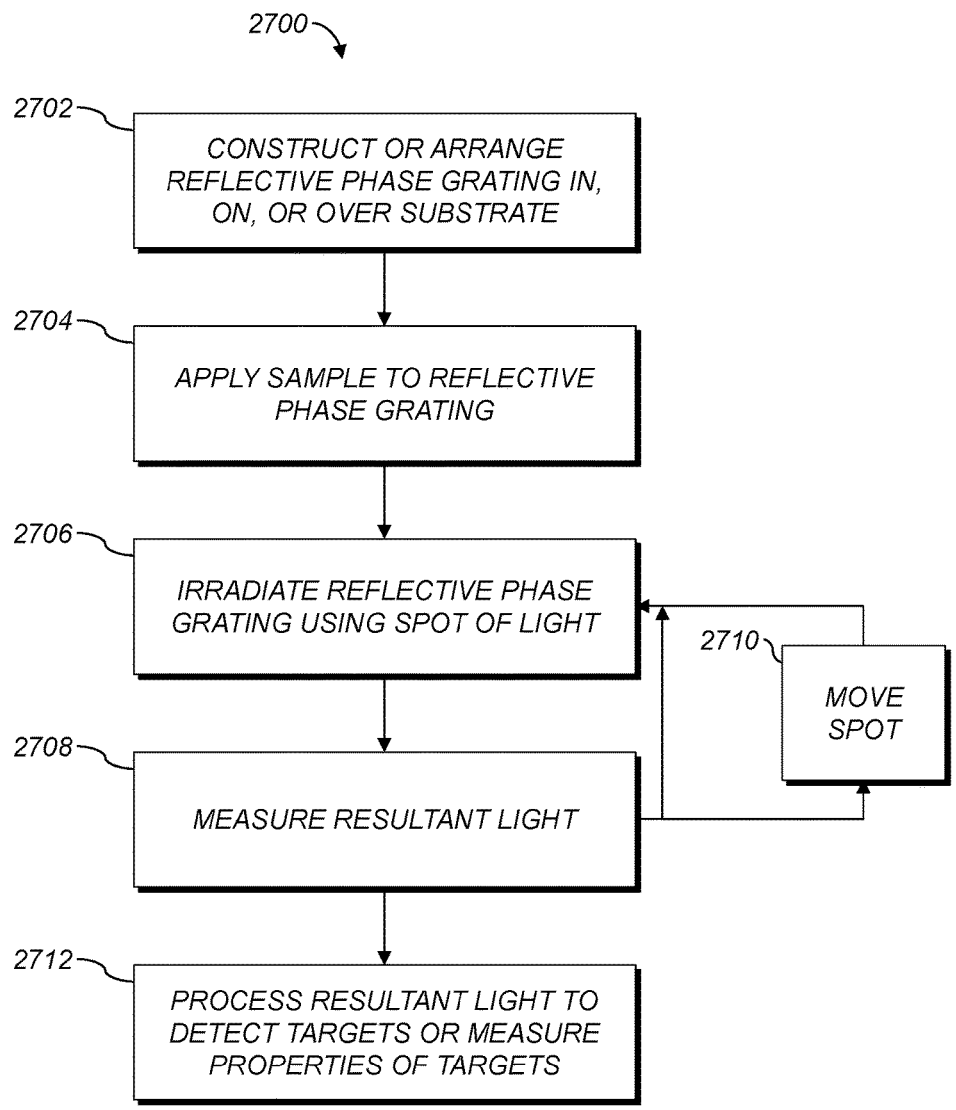
FIG. 27 is a flow diagram of an example process for detecting a target.

FIG. 27 is a flow diagram of an example process 2700 for detecting a target. Processing can begin with block 2702 or block 2704.

At block 2702, a reflective phase grating can be constructed or arranged in, on, or over a substrate. For example, a disc-format LOC can be constructed using PTM plus metallization, as described above.

At block 2704, a sample, e.g., a fluidic sample such as a liquid sample, can be applied to the reflective phase grating (or to another reflective surface, and likewise throughout). Examples are discussed above, e.g., with reference to blocks 2402-2406, 2502, or 2602.

At block 2706, the reflective phase grating can be irradiated, e.g., using a focused spot of light such as a laser spot. Examples are discussed above, e.g., with reference to blocks 2408 or 2504.

At block 2708, resultant light can be measured. Block 2708 can be followed by block 2706, block 2710 or block 2712. This can permit scanning, e.g., across the reflective surface or in focal depth, as described herein.

At block 2710, the spot of light can be moved with respect to the sample, e.g., with respect to the reflective grating. Examples are discussed above, e.g., with reference to blocks 2606-2612, FIG. 1-16, 18, 19, 22, or 23, or Tables 2, 3, or 6.

Figure 30:
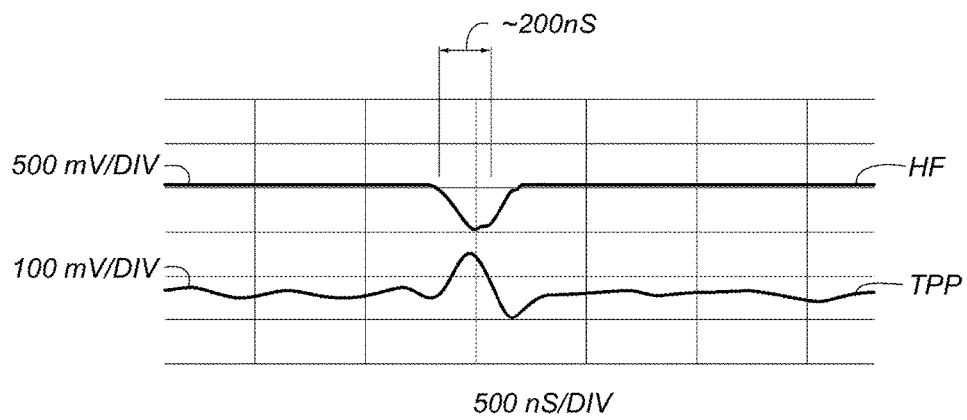
FIG. 30 shows measured data of 100 nm gold nanoparticles.
Figure 31:
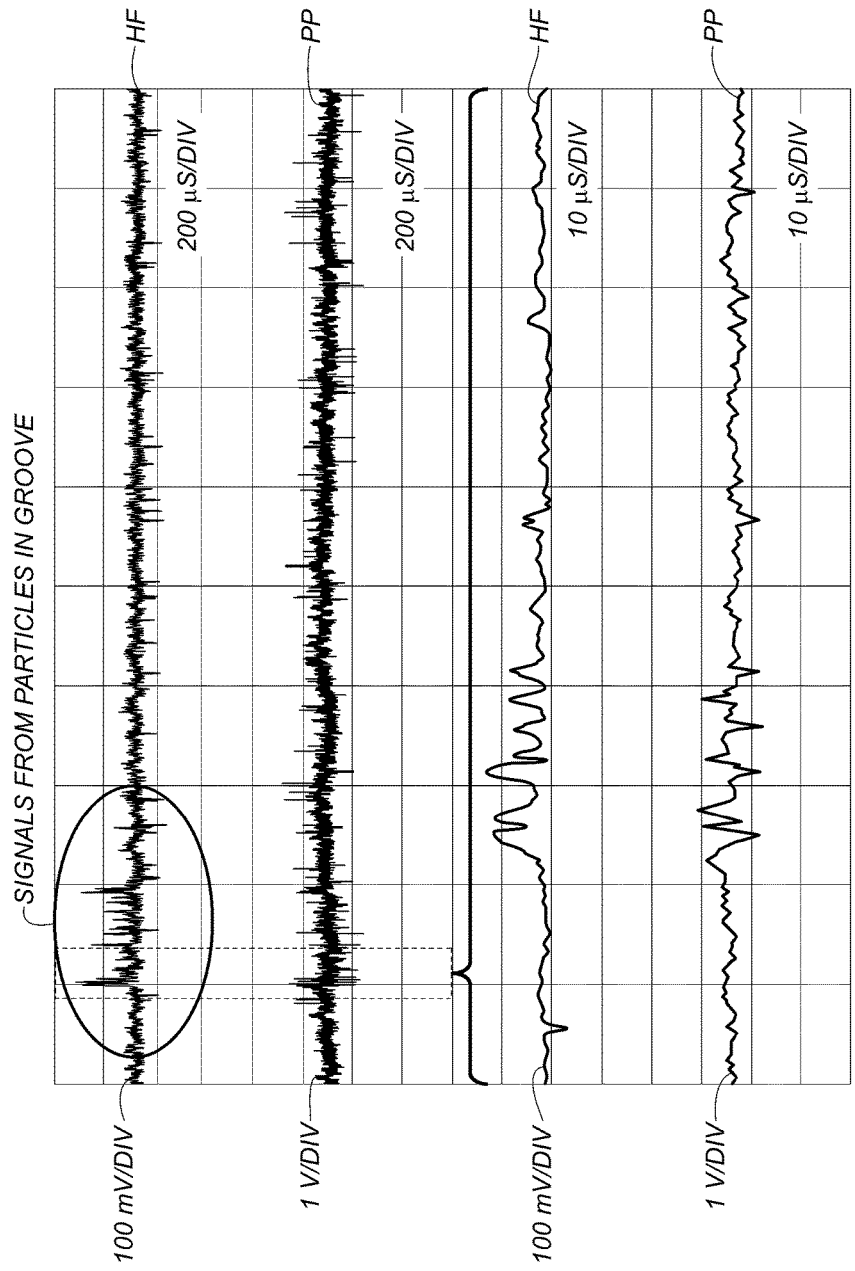
FIG. 31 shows measured data of particles in a groove of a reflective grating.

At block 2712, the detected resultant light can be processed to detect targets or to measure properties of the targets. For example, HF and PP signals coinciding in time, e.g., as shown in FIGS. 30 and 31, discussed below, can indicate presence of a target. For example, the duration of a PP signal in time can indicate the size of a target. Examples are discussed herein, e.g., with reference to blocks 2408, 2506, or 2604, or FIG. 7, 11, 15, 17, 19-21, or 28-33.

Figure 28:
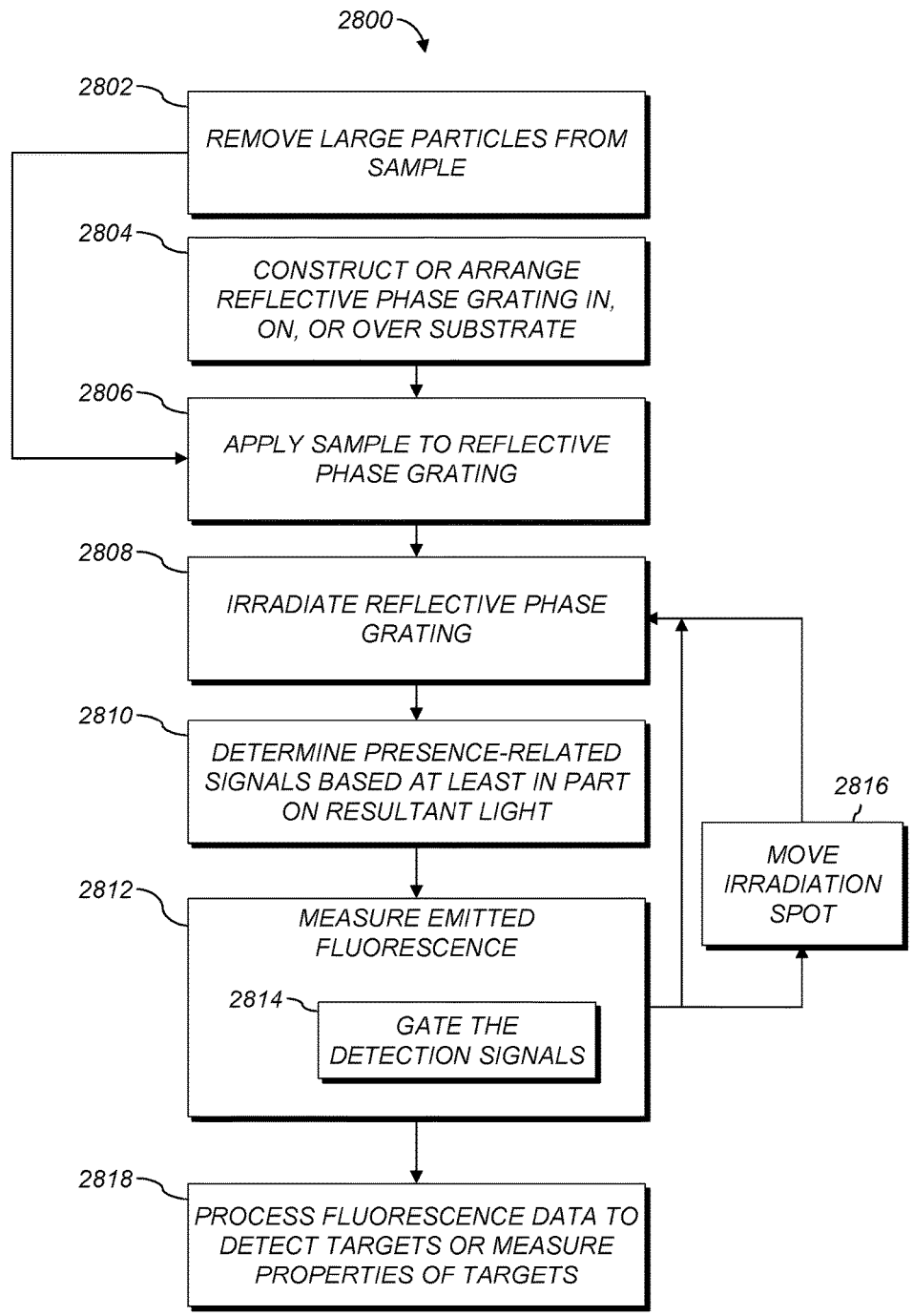
FIG. 28 is a flow diagram of an example process for analyzing a sample.

FIG. 28 shows a flowchart 2800 of example methods of analyzing a sample.

At block 2802, particles of selected size range(s) can be removed from a sample. For example, samples can be centrifuged, filtered, fractionated, or otherwise divided into portions based on particle size. For example, large particles can be removed from a sample to permit analysis of small particles remaining in the sample. Examples are discussed above, e.g., with reference to FIG. 1 or 7. Block 2802 can be followed by block 2806.

At block 2804, a reflective phase grating can be constructed or arranged in, on, or over a substrate. For example, grooves can be etched into a slide, or a BLU-RAY or other disc-format LOC can be prepared using stamping with a PTM master as described herein, e.g., with reference to FIG. 3.

At block 2806, a sample can be applied to, disposed over, or received at the reflective phase grating. This can be done, e.g., using a micropipette. Examples are discussed above, e.g., with reference to blocks 2402-2406, 2502, or 2704.

At block 2808, the reflective phase grating can be irradiated, e.g., using a laser, lamp, LED, or other light source. Focusing or collimating optics can additionally be used. Examples are discussed above, e.g., with reference to blocks 2408, 2504, or 2706.

At block 2810, presence-related signals, e.g., representing or otherwise based at least in part on resultant light, can be determined, e.g., by detecting or measuring resultant light. Presence-related signals can include HF, RPP, TPP, or other signals useful for determining whether or when a target is being irradiated. In some examples, before, concurrently with, or in addition to measuring fluorescence, non-fluorescence or other additional signal(s) are measured to determine, e.g., presence, size, shape, or volume of a target or other particle being irradiated. In some examples, the number of particles or the sizes and shapes of individual particles are measured, and fluorescence data from some of the particles are measured, e.g., to determine the origins of the particles. Examples are discussed above, e.g., with reference to blocks 2408, 2506, 2604, or 2708.

In some examples, block 2810 can include measuring HF or PP signals in a reference area. The reference area can include, e.g., a mirror (non-grooved) area of a disc or LOC, or an area with grooves. The reference area can be substantially free of samples or targets. Block 2810 can include measuring the HF or PP signals in the detection region and determining a variation of the measured signal from the previously-measured signal in the reference area. In some examples, variations between a reference signal and a corresponding signal measured in a sample indicate the presence of targets, EVs, or other microparticles in the sample, e.g., as discussed herein with reference to FIGS. 11-27.

At block 2812, emitted fluorescence or other reflected, transmitted, emitted, or scattered light can be measured, e.g., using a pPMT or other sensors described herein. This can be done, e.g., when or during a period in which the presence-related signals indicate a target is being irradiated. This can reduce mis-identification as target-related of photons not from a target. Examples are discussed above, e.g., with reference to block 2604 or FIG. 15.

At block 2814, detection signals from a pPMT or other sensors can be gated. For example, gating can be performed as discussed above with reference to FIGS. 19-21. Although shown as part of block 2812 for purposes of explanation, functions performed at block 2814 can be performed before or after functions performed at block 2812. For example, gating can be performed in the analog domain on pPMT or amplifier (FIG. 17) outputs, or can be performed in the digital domain on digitized representations of those outputs.

At block 2816, the location of irradiation ("irradiation spot") can be moved, i.e., relative motion of an irradiation spot and the reflective phase grating can be caused. For example, a laser can be redirected, e.g., rasterized across the sample, or the sample can be moved, e.g., by the spinning of a disc over a laser or other irradiation source substantially fixed in tangential position with respect to the axis of rotation of the disc. A spot-traversal system can cause such relative motion, and can include one or more of the following: rasterizers; polygons or other movable mirrors; mirror or micromirror arrays; fixed mirrors; rotational, linear, XY, or XYZ stages or drives; lenses; or gratings. Examples are discussed above, e.g., with reference to FIG. 22 or blocks 2606-2612 or 2710.

At block 2818, data of the detected fluorescence can be processed to detect targets or measure properties of targets, e.g., as described herein. For example, detected photon signals can be gated, e.g., as described herein. Example gating can be performed based at least in part on HF and TPP signals, e.g., as in FIGS. 19-21. Pulse heights can be measured and recorded, e.g., in histogram bins, or pulses can be counted. Examples are discussed above, e.g., with reference to FIG. 1,11,13-15, 20, or 21.

In some examples, at block 2818, measured, estimated, or computed refractive indices of at least one of the medium (e.g., blood plasma or air), the target, or a portion of the target can be used in computing sizes of the targets. Various aspects use fluorescent dyes or a pre-check to distinguish targets from, e.g., surface defects, dust particles, non-target air bubbles, or other microstructures that are not targets to be measured. In some examples, the pre-check includes measuring data before applying targets to the reflective phase grating, e.g., to detect, e.g., nanometer-scale defects in the substrate.

Targets can be detected using a rotating reflective grating and an irradiation spot. Targets can also be detected using a focused scanning spot in combination with a flow cell, e.g., as described herein with reference to FIG. 1-6 or 10-16. In some examples, the pitch of the phase grating can be set to approximately twice the size of the targets to be detected. In some examples, the refractive indices of the sample and the target can be used to determine the particle size from the pulse width or height of the HF or PP signals.

Some example parameters for various formats of LOCs or measurement thereof are given in Table 6, below. Illustrative axes are r (radial position on a disc), A (angular position on a disc, X/Y (Cartesian coordinates on a disc or chip), or v (position along a flow axis of a flowing sample).

TABLE 6

| Parameter | Disc Format | Chip Format |
| --- | --- | --- |
| Scanning Axes | r-θ | r-θ, X-Y, or X-v (v = flow axis) |
| Shape | disc | disc, rectangle, or flow cell |
| Pattern 1 | Pit, Track, Mark | Phase Scale or Mirror |

TABLE 6-continued

| Parameter | Disc Format | Chip Format |
|---|---|---|
| Pattern 2 | Spiral | Spiral, Concentric, Parallel, None |
| Signal Dimension | Fix on plane | Three-dimension in gap channel |
| Signal Source 1 | Embossed Depth | Particle in carrier fluid (liquid/gas) |
| Signal Source 2 | Surface | Volume within focus depth |
| Cover Refractive Index | Uniform RI | Multiple refractive indices (RIs), e.g., three RIs |
| Main signal | HF | TPP + FL |
| Cover thickness | 1.2 mm (CD), 0.6 mm (DVD), 0.1 mm (BLU-RAY) | 0.12 mm (microscope slide) or other formats |

In some nonlimiting examples, an LOC as described herein does not include data-storage structures such as pits, lands, embedded dyes, or other structures used to record information on optical discs. In some examples, an LOC as described herein comprises a mirror or other substantially non-pitted or non-grooved reflective surface. In some examples, the size of the focused spot is calibrated to provide a scale for the detected particles (e.g., spot width in meters can be related to scan speed in m/s and pulse width in seconds to determine target size). In some examples, a reflective phase grating is configured with pitch and groove depth (or land height) to provide gain under desired optical configurations. In some examples, the focused spot is smaller than the width of a groove or is smaller than the width of a land.

Some examples include one or more of the following: (a) reflective grating or optics are scaled for particle size, e.g., the pitch, irradiation system, or lens are selected to maintain $p \geq \lambda/2NA$ as described herein; (b) reflective grating has a 1:1 aspect ratio L:G; (c) groove depth is $\lambda/8n$, where n is the refractive index of the fluid sample containing the targets; (d) grating pitch is decided by particle size and spot size; (e) spot size is <2 μm FWHM; (f) channel gap is approximately equal to the focus depth; (g) channel gap is less than eight times the focus depth; (h) a mirror use used and the size of the focused spot provides scale information for determining particle size; (i) the spot is scanned over the sample, e.g., to count particles/unit volume; (j) scanning is configured as at least one of r-θ, X-Y, or X-v; or (k) the targets are ≥10 nm.

Illustrative Results and Further Illustrative Examples

In some examples, drops of liquid were placed on the disc discussed above with reference to FIG. 10. The drops were added to regions 1004. The drops were permitted to dry for 3-8 min, forming a drop area of 5-6 mm². The drops included 170 nm polystyrene beads. A concentration of $\sim 3 \times 10^9$/mL was tested.

Some tested example configurations used disc-format LOCs such as the LOC shown in FIG. 10. In some examples, a traverse signal was captured with the disc rotating but with no tracking. The focus servo was active. A traverse signal was captured with the irradiation spot scanning radially at a fixed speed).

In a tested example, at 1 m/s scanning velocity, a pulse width of a measured pulse was substantially equal to FWHM spot size: 240 nm, or 240 ns at 1 m/s, using a BLU-RAY laser spot of λ=405 nm. The measurement time per particle was ~0.25 μs/particle. In some examples, the irradiation spot has a diameter <2 μm FWHM.

Figure 29:
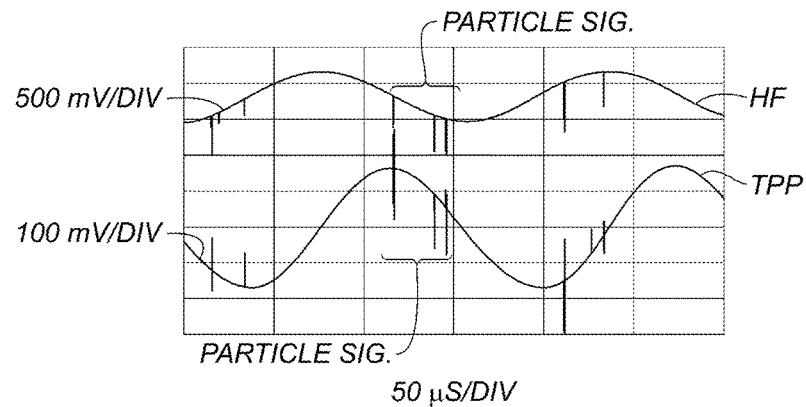
FIG. 29 shows measured data of 100 nm gold nanoparticles.

FIG. 29 shows measured data of 100 nm gold (Au) nanoparticles detected at a spot-scanning speed of 1.4 m/s. The scanning speed of 1.4 m/s was the linear velocity of the spot with respect to the disc. Experiments were performed with nanoparticles in a liquid sample. Gold and polymer particles were tested. Gold 100 nm particles showed clear pulse signals with 30% modulation amplitude and particles as small as 30 nm showed detectable signal. In this configuration, laser beam illuminates individual particles at appropriate concentration.

FIG. 30 shows measured data of 100 nm gold (Au) nanoparticles detected at a spot-scanning speed of 1.4 m/s. As shown, the nanoparticle produced a detectable signal having a width of approximately 200 ns.

Further experiments were performed to evaluate particle detection in a liquid environment. A 2 μm gap microchannel was formed on a phase grating surface of a disc and sealed by 100 μm cover glass with a 500 μm diameter sample inlet made in a 1.1 mm-thick polymer supporting substrate. A similar structure is discussed herein with reference to FIG. 1. The sample liquid filled the micron-gap well by capillary action in an air atmosphere. 100-nm gold particles in water were detectable by modulation, and spatial resolution was confirmed for k-dominant gold particles.

FIG. 31 shows measured data of a tested example. Waveforms are shown for particles detected in grooves of a reflective phase grating. A laser wavelength λ=405 nm, a lens with numerical aperture NA=0.85, and a disc with a cover thickness of 0.1 mm were used. Other λ, NA, and cover-thickness values can also or alternatively be used. Lower λ or higher NA values can permit detecting smaller targets than higher λ or lower NA values.

Figure 32:
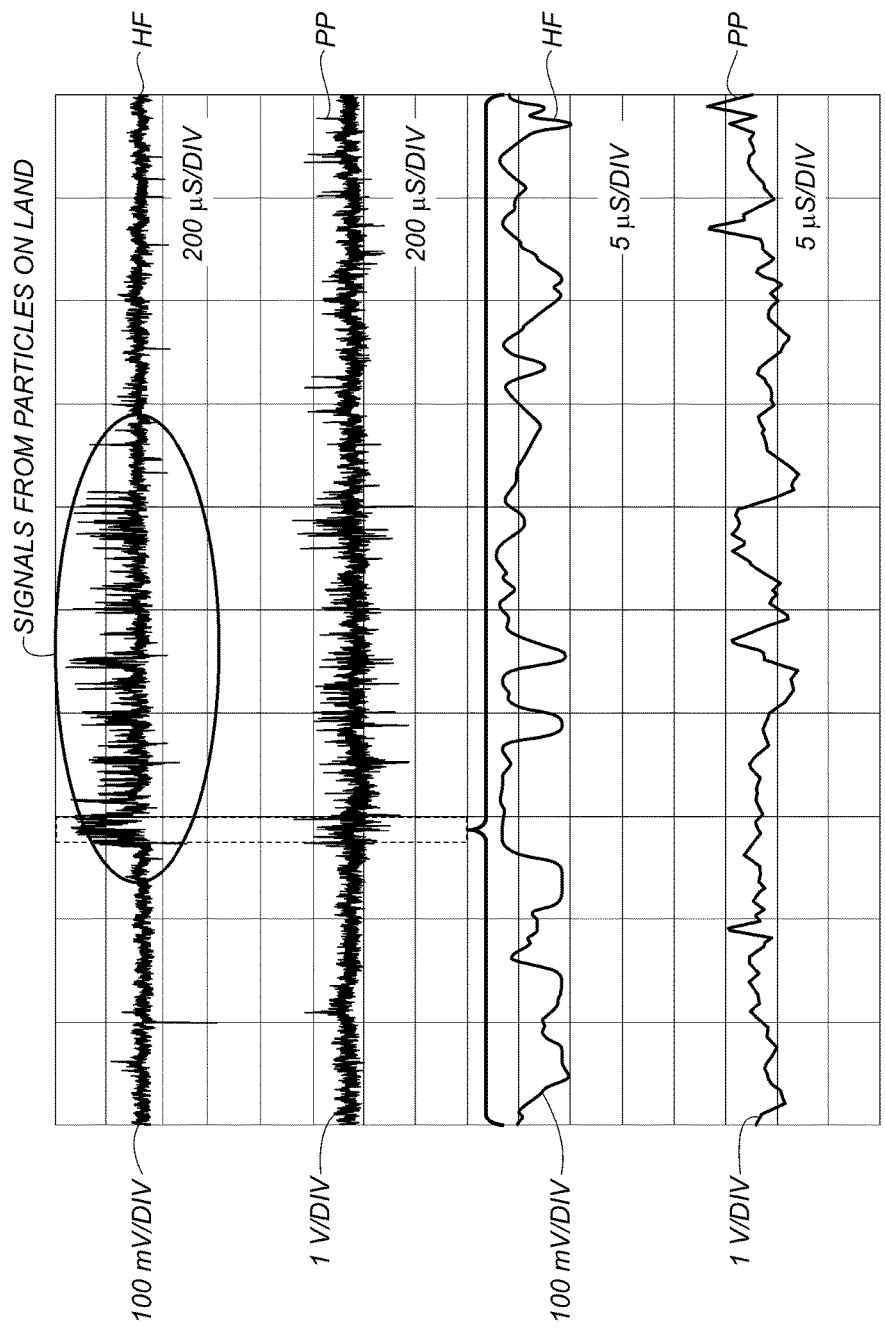
FIG. 32 shows measured data of particles on a land of a reflective grating.
Figure 33:
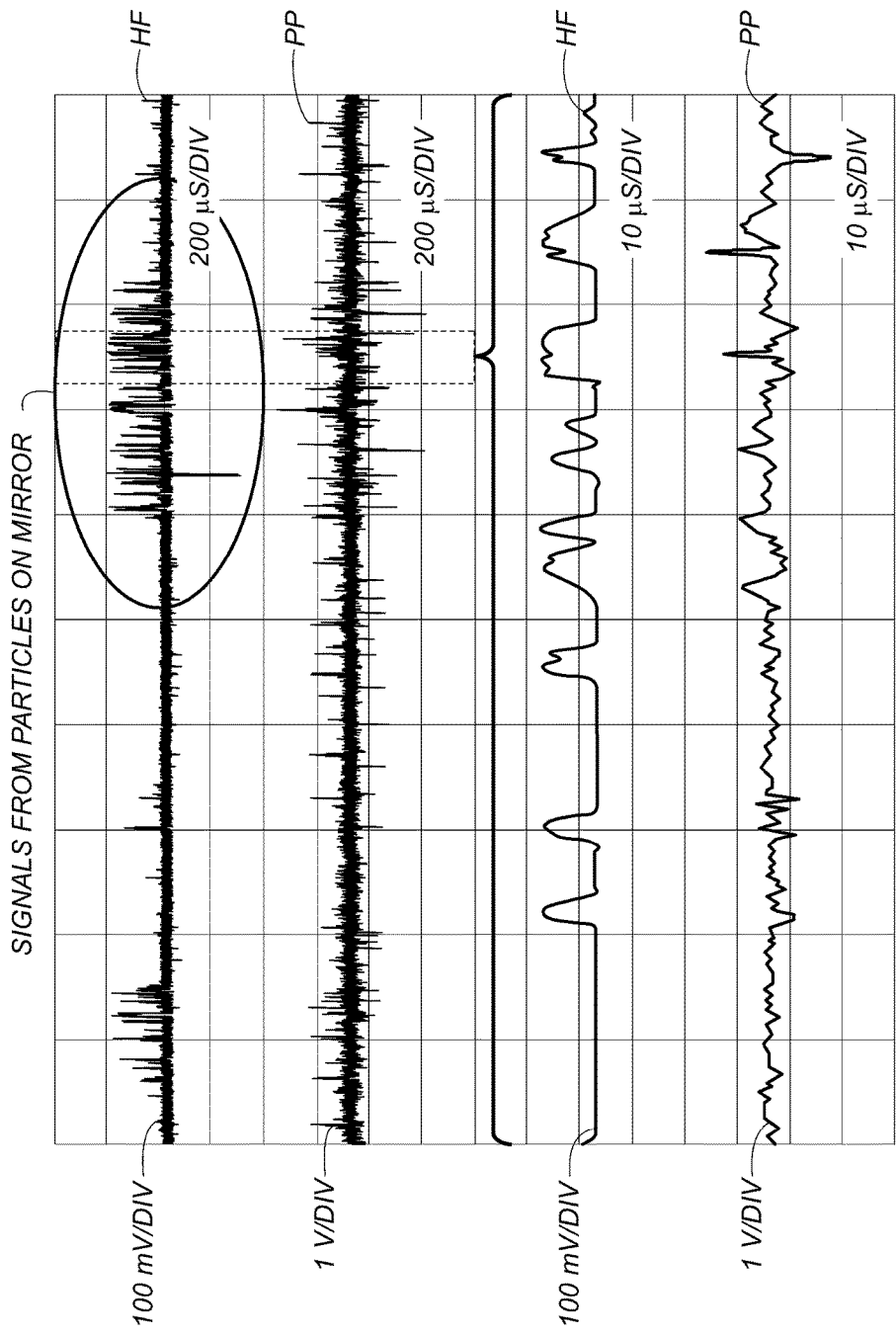
FIG. 33 shows measured data of particles on substantially flat reflective surface ("mirror").

In FIG. 31, and also in FIGS. 32 and 33, HF and radial PP signals are shown. The bottom half is a magnification of the indicated portion on the top half. The dashed box shows signals that were measured of a target. The amplitude of modulation of the measured signal, compared to (e.g., divided by) the peak-to-peak excursion of that signal, is correlated with the optical path length $\Delta n \times d$ of the target, where $\Delta n$ is the refractive-index difference between the particle and the medium around it, and d is the size of the particle (e.g., mean diameter). In some examples, $\Delta n$ is measured with reference to the polymer material of the disc. In some examples, the medium is selected to have a different refractive index than the disc, the particles, or both. In some example, the substrate has n=1.50, the targets have n=1.53, and the sample has n=1.58 ($\Delta n$=0.05).

FIG. 32 shows measured data of a tested example. Waveforms are shown for particles detected on lands of a reflective phase grating.

FIG. 33 shows measured data of a tested example. Waveforms are shown for particles detected on a reflective surface substantially without a grating ("mirror").

Figure 34:
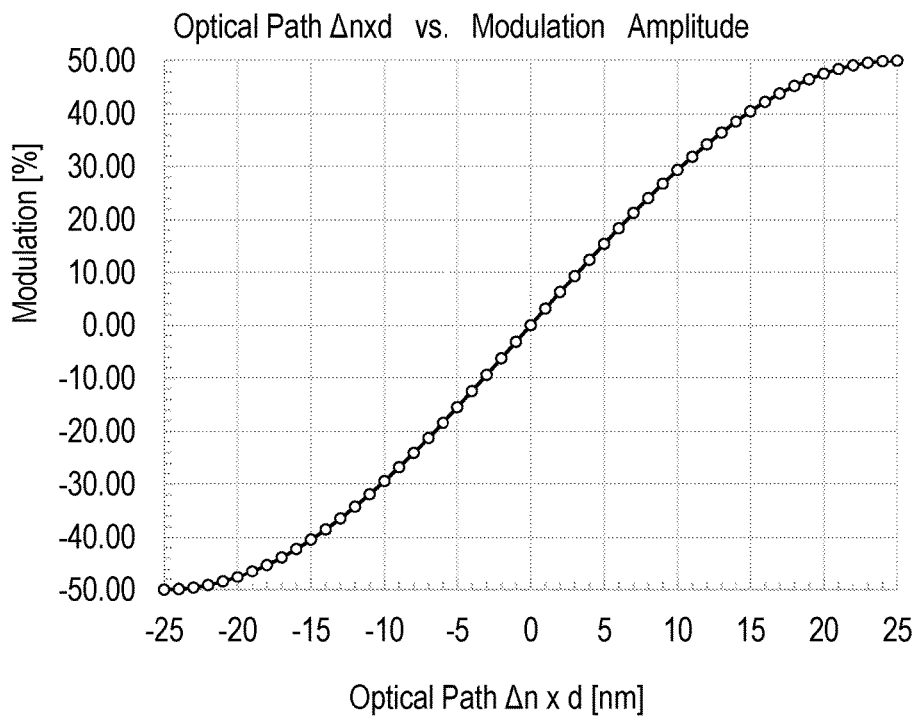
FIG. 34 is an example plot of modulation amplitude by optical path difference.

FIG. 34 shows an example plot correlating optical path distance change ($\Delta n \times d$) with modulation amplitude (percent). In some examples, the pulse width of an HF or TPP pulse times the scanning velocity of the spot with respect to the target can be an estimate of the tangential size of particle. The RPP pulse height can be correlated with radial size, or the TPP pulse height can be correlated with tangential size. In an example of a 100 nm particle having n=1.592, a PP signal of 0.85V with a modulation $\Delta PP/PP$=28% gives a $\Delta n \times d$ of 8 nm, so d=8 nm, $\Delta n$=8 nm/0.05, giving an estimate, to a first order, of 160 nm. In some examples, for HF-signal noise ~50 mV, $\Delta n$>=~0.035 can be measured, e.g., particles as small as 6 nm in some examples.

In some examples, RPP and TPP pulses can be detected for a particular target (e.g., temporally overlapping RPP and TPP pulses). The extents of the particle in radial and tangential directions can be determined. A two-dimensional image of the target can be determined from the extents. These determinations can be performed for multiple targets, and a two-dimensional image of the targets with respect to each other can be determined from the extents of the particles and the relative timings of the signals, which are correlated with the relative positions of the targets.

In some examples, PP signals have high gain when the groove depth of a reflective grating is $\lambda/8n$. In some examples, HF signals have high gain when the groove depth of a reflective grating is $\lambda/4n$. In some examples, a grating has a groove depth of $\lambda/8n$ or $\lambda/4n$. In some examples, a detection system and reflective phase grating are configured for use with $\lambda=405$ nm and $n=1.33$, e.g., for aqueous samples. Accordingly, groove depth can be, e.g., $\lambda/8n=38.0$ nm or $\lambda/4n=76.1$ nm. The PP signal can be measured to detect double-pass phase shift due to the presence of a target. The optical path difference due to target can be, e.g., $\Delta\varphi=\Delta n \times thickness \times 2$. The modulation depth by a target can this be, or be proportional to, $\sin(\pi/2 \times 4/(\lambda/8))$.

In some examples, a microvesicle has a diameter of ~100 nm. The microvesicle can include a lipid bilayer surface with a thickness of ~10 nm and $n=1.48$ surrounding an aqueous core with $n=1.38\pm0.02$. The microvesicle target can be included in a water sample with $n=1.333$. In some examples, reflective surface 2202 (e.g., the surface of a reflective phase grating) can include Al with $n=0.879$ and $k=2.984$, at a thickness of, e.g., ~50 nm-~100 nm. Cover 2314 can include glass or polymer with $n=~1.46-~1.65$ and a thickness of 100 µm±3 µm.

Some experiments detected a 170 nm coated bead arranged in a pressure-sensitive adhesive (PSA) layer. Some experiments detected a 170 nm polystyrene (PS) bead. Some experiments detected a 100 nm bead in air. Some experiments detected a 70 nm polymer nanoparticle in air. Some experiments detected 50 nm Au nanoparticles or 30 nm Au nanoparticles. Some of these experiments used only the HF signal to detect the nanoparticles. In some examples, HF pulse height was correlated with particle size.

Some experiments had a noise limit of approximately 30 nm, corresponding to 34 mV of noise and 200 mV of signal for a 170 nm bead. Some experiments had a noise limit of ~10 nm, corresponding to a 5.5 V(pk-pk) TPP signal and 0.22 V(pk-pk) of noise for a 250 nm target. In some experiments, TPP signals or RPP signals were detected.

A reflective grating and focused scanning spot together provided effective detection of targets, e.g., vesicles or nanoparticles. In some experiments, the number of particles was countable by the number of pulses, e.g., of the HF signal. In some experiments, particle size was correlated with the pulse width and modulation depth of the HF and PP signals.

Example Clauses

A: A measurement system comprising a reflective phase grating, a light source, a motion system configured to induce relative motion of the light source and the phase grating, and a detection system configured to detect light reflected by the phase grating.

B: The system according to paragraph A, further including a cover spaced apart from the reflective phase grating.

C: The system according to paragraph A or B, further including a sample inlet.

D: The system according to paragraph C, further including a vacuum port.

E: The system according to paragraph D, wherein the vacuum port and the sample inlet are arranged on opposite sides of a measurement area, e.g., a detection region, including the reflective phase grating.

F: The system according to any of paragraphs A-E, further including a vacuum port.

G: A measurement device comprising a substrate and a reflective phase grating arranged on, in, or over the substrate.

H: The device according to paragraph G, further including a cover spaced apart from the reflective phase grating.

I: The device according to paragraph G or H, further including a sample inlet.

J: The device according to paragraph I, further including a vacuum port.

K: The device according to paragraph J, wherein the vacuum port and the sample inlet are arranged on opposite sides of a measurement are, e.g., a detection region, including the reflective phase grating.

L: The device according to any of paragraphs G-K, further including a vacuum port.

M: A method of measuring, comprising irradiating a reflective phase grating and measuring reflected light.

N: The method according to paragraph M, further including disposing a sample over the reflective phase grating or receiving a sample at the reflective phase grating.

O: The method according to paragraph M or N, further including causing relative motion of an irradiation spot and the reflective phase grating.

P: A measurement system, comprising: a spot-traversal system for causing relative motion of a sample and an irradiation spot, wherein the sample includes one or more fluorescent markers having respective fluorescence wavelengths; and an optical detection system configured to detect fluorescent light from at least some of the fluorescent markers irradiated by the irradiation spot.

Q: The system according to paragraph P, wherein the fluorescent markers include fluorescent-dyed anti-bodies configured to conjugate with molecules of interest in the sample, or include fluorescent tags configured to conjugate with the molecules of interest.

R: The system according to paragraph P or Q, wherein the irradiation spot includes a focused laser spot with a full-width at half maximum diameter smaller than fourteen microns or fourteen hundred nanometers.

S: The system according to any of paragraphs P-R, the optical detection system configured to detect light at each of a plurality of wavelengths and the system further including a spectral discriminator arranged between the sample and the optical detection system, the spectral discriminator configured to provide light at wavelength(s) of the plurality of wavelengths to the optical detection system.

T: The system according to paragraph S, wherein the spectral discriminator includes at least one of a dichroic mirror, a grating, a prism, a filter, or a polychromator.

U: The system according to any of paragraphs P-T, wherein the optical detection system is configured to detect single photon pulses without averaging.

V: The system according to any of paragraphs P-U, further including a tracking system configured to provide one or more tracking signals based at least in part on resultant light substantially at a wavelength of the irradiation spot, wherein the optical detection system is configured to gate detected photon signals based at least in part on one(s) of the tracking signal(s).

W: The system according to paragraph V, wherein the gating is based at least in part on a high-frequency (HF) tracking signal, a tangential push-pull (TPP) signal, or both.

X: The system according to any of paragraphs P-W, further comprising a reflective phase grating over which the sample is arranged.

Y: The system according to paragraph X, further including a cover spaced apart from the reflective phase grating.

Z: The system according to any of paragraphs P-Y, further including a sample inlet.

AA: The system according to any preceding system paragraph, further including a vacuum port.

AB: The system according to paragraph AA, wherein the vacuum port and the sample inlet are arranged on opposite sides of a measurement area including the reflective phase grating.

AC: A method of measuring, comprising irradiating a reflective phase grating measuring resultant light in a selected wavelength range, and gating the measured light based at least in part upon a tracking signal.

AD: The method according to paragraph AC, further including disposing a sample over the reflective phase grating or receiving a sample at the reflective phase grating.

AE: The method according to paragraph AC or AD, further including causing relative motion of an irradiation spot and the reflective phase grating.

AF: An assembly, comprising: a target holder configured to retain a target in a detection region, wherein the target holder comprises a reflective surface configured to reflect at least part of a focused spot of light to provide resultant light; an irradiation system configured to irradiate at least part of the detection region with the focused spot of light; a motion system configured to cause motion of the focused spot of light relative to the reflective surface; and a detection system configured to detect the resultant light.

AG: The assembly according to paragraph AF, wherein: the irradiation system is configured to provide the focused spot of light, which comprises light of a predetermined wavelength; the irradiation system comprises a lens having a predetermined numerical aperture and arranged to focus the light of the predetermined wavelength to provide the focused spot of light; and the reflective grating has a pitch exceeding a reference pitch substantially equal to a result of dividing the predetermined wavelength by twice the predetermined numerical aperture.

AH: The assembly according to paragraph AF or AG, wherein: the irradiation system is configured to provide the focused spot of light, which comprises light of a predetermined wavelength; and the detection system comprises at least one optical detector configured to detect light of a different wavelength than the predetermined wavelength.

AI: The assembly according to any of paragraphs AF-AH, further comprising a sample-delivery system configured to apply a sample comprising the target to the at least part of the detection region.

AJ: The assembly according to any of paragraphs AF-AI, further comprising a sample-delivery system configured to apply a fluidic sample comprising the target to the at least part of the detection region.

AK: The assembly according to paragraph AJ, wherein: the reflective surface comprises a reflective grating; the irradiation system is further configured to provide the focused spot of light, which comprises light of a predetermined wavelength; the irradiation system comprises a lens having a predetermined numerical aperture and being arranged to focus the light of the predetermined wavelength to provide the focused spot of light; the reflective grating has a pitch exceeding a reference pitch substantially equal to a result of dividing the predetermined wavelength by twice the numerical aperture; the fluidic sample comprises a fluid having a predetermined refractive index; and the reflective grating includes at least one groove having a depth substantially between a first reference value and a second reference value, the first reference value being the result of dividing the predetermined wavelength by the product of sixteen and the refractive index and the second reference value being substantially three times the first reference value.

AL: The assembly according to paragraph AJ or AK, wherein the sample-delivery system is configured to apply the fluidic sample, which comprises a liquid.

AM: The assembly according to any of paragraphs AJ-AL, further comprising a flow system, e.g., a vacuum pump or fluid pump, configured to move the fluidic sample through the detection region.

AN: The assembly according to any of paragraphs AJ-AM, wherein the fluidic sample comprises a fluid having a predetermined refractive index and the irradiation system is configured to provide the focused spot of light comprising light of a predetermined wavelength.

AO: The assembly according to paragraph AN, wherein the reflective grating includes at least one groove having a depth substantially equal to a result of dividing the predetermined wavelength by eight times the predetermined refractive index.

AP: The assembly according to paragraph AN or AO, wherein: the assembly further comprises a fluid channel at least partly overlapping with the at least part of the detection region; and the irradiation system is configured to provide the light substantially in an irradiation direction.

AQ: The assembly according to paragraph AP, wherein the channel has a height substantially along the irradiation direction substantially equal to a result of dividing the predetermined wavelength by eight times the predetermined refractive index.

AR: The assembly according to paragraph AP or AQ, wherein the channel has a height substantially along the irradiation direction substantially between a first reference value and a second reference value, the first reference value being the result of dividing the predetermined wavelength by the product of sixteen and the predetermined refractive index and the third reference value being substantially three times the first reference value.

AS: The assembly according to any of paragraphs AJ-AR, wherein the flow system is configured to cause the fluidic sample to move through the at least part of the detection region at least substantially in a flow direction, and the motion system is configured to concurrently cause relative motion of the focused spot of light in a second direction different from (e.g., substantially perpendicular to) the first direction.

AT: The assembly according to any of paragraphs AF-AS, wherein: the detection system comprises at least one split photodetector configured to provide a plurality of detection signals; and the assembly further comprises a data-processing system configured to determine, based at least in part on at least two of the plurality of detection signals, at least one of a sum signal, a transverse push-pull signal, or a radial push-pull signal.

AU: The assembly according to paragraph AT, further comprising a gating system configured to provide a particle signal associated with a temporal overlap between a first signal of the plurality of detection signals and a second, different signal of the plurality of detection signals.

AV: The assembly according to paragraph AU, wherein the first signal comprises the sum signal and the second signal comprises the transverse push-pull signal.

AW: The assembly according to any of paragraphs AT-AV, wherein: the irradiation system is further configured to provide the focused spot of light, which comprises light of a predetermined wavelength; and the detection system further comprises at least one optical detector configured to detect light of a different wavelength than the predetermined wavelength and to provide a detection signal corresponding to the light of the different wavelength.

AX: The assembly according to paragraph AW, further comprising a gating system configured to provide a particle signal associated with a temporal overlap between at least one of the plurality of detection signals and the detection signal corresponding to the light of the different wavelength.

AY: The assembly according to paragraph AX, further comprising a counter configured to count discrete occurrences of the particle signal.

AZ: The assembly according to any of paragraphs AW-AY, wherein the different wavelength is a wavelength longer than the predetermined wavelength.

BA: The assembly according to any of paragraphs AF-AZ, wherein: the reflective surface comprises a reflective grating having at least one groove; and the motion system is further configured to cause relative motion of the focused spot of light substantially across the at least one groove.

BB: The assembly according to any of paragraphs AF-BA, wherein the reflective surface comprises a reflective grating having at least one groove.

BC: The assembly according to paragraph BB, wherein the motion system is further configured to cause relative motion of the focused spot of light substantially along the at least one groove.

BD: The assembly according to paragraph BC, wherein the motion system is further configured to rotate the reflective surface to define a tangential direction of the rotating reflective surface, and to concurrently translate the focused spot of light substantially in a direction different from the tangential direction to track the focused spot of light substantially along the at least one groove.

BE: The assembly according to any of paragraphs AF-BD, wherein the motion system is further configured to cause relative motion of the focused spot of light in two different (e.g., substantially perpendicular) directions over the reflective surface.

BF: The assembly according to any of paragraphs AF-BE, wherein the motion system is further configured to cause motion of the reflective surface in a first direction and to concurrently cause relative motion of the focused spot of light in a second direction different from (e.g., substantially perpendicular to) the first direction.

BG: The assembly according to any of paragraphs AF-BF, wherein the motion system is further configured to cause motion of the reflective surface and to concurrently maintain a focus of the focused spot of light with respect to the reflective surface.

BH: The assembly according to any of paragraphs AF-BG, wherein the reflective surface comprises a substantially flat reflective surface.

BI: The assembly according to any of paragraphs AF-BH, wherein the motion system is further configured to adjust a focal position of the focused spot of light along an axis substantially normal to at least a portion of the reflective surface.

BJ: A device, comprising: a substrate; a sample inlet associated with the substrate; and a reflective grating associated with the substrate, wherein: the reflective grating is configured to retain a fluidic sample in a detection region; the detection region is fluidically connected to the sample inlet; and the detection region is operatively arranged with respect to the reflective grating so that at least a portion of light passing through the detection region towards the reflective grating also passes through the detection region after reflecting off the reflective grating.

BK: The device according to paragraph BJ, wherein the fluidic sample comprises a liquid.

BL: The device according to paragraph BJ or BK, further including an outlet fluidically connected to the detection region and spaced apart from the sample inlet.

BM: The device according to any of paragraphs BJ-BL, further including a cover spaced apart from the reflective grating and arranged so that the detection region is at least partly between the reflective grating and the cover, wherein the cover is at least partly transparent to the at least a portion of the light.

BN: The device according to any of paragraphs BJ-BM, further comprising a reservoir fluidically connected to the detection region and spaced apart from the sample inlet.

BO: The device according to paragraph BN, wherein the reservoir has a volume exceeding a sum of a volume of the sample inlet and a volume of the detection region.

BP: The device according to any of paragraphs BJ-BO, wherein the reflective grating comprises at least one groove, and the at least one groove comprises at least two of: a spiral groove portion, a straight groove portion, or a circular groove portion.

BQ: The device according to paragraph BP, wherein the at least one groove comprises a first groove and a second groove, the first groove comprises at least a first one of the spiral groove portion, the straight groove portion, and the circular groove portion, and the second groove comprises at least a second, different one of the spiral groove portion, the straight groove portion, and the circular groove portion.

BR: The device according to any of paragraphs BJ-BQ, wherein: the sample inlet is configured to receive a provided sample; and the device further comprises a filter element operatively arranged to filter the provided sample to provide the fluidic sample.

BS: The device according to any of paragraphs BJ-BR, wherein the substrate is a disc-format substrate.

BT: The device according to any of paragraphs BJ-BS, wherein the sample inlet is one of a plurality of spaced-apart sample inlets of the device; the detection region is one of a plurality of detection regions of the device; and the device further comprises one or more spaced-apart vacuum ports; wherein individual detection regions of the plurality of detection regions are fluidically connected to at least one of the one or more vacuum ports and are fluidically connected to at least one of the plurality of sample inlets.

BU: The device according to paragraph BT, further comprising a vacuum channel fluidically connected to at least one of the one or more spaced-apart vacuum ports.

BV: The device according to paragraph BT or BU, wherein at least one of the vacuum ports is arranged on an opposite side of the detection region from at least one of the sample inlets.

BW: The device according to any of paragraphs BJ-BV, wherein: the sample inlet is one of a plurality of spaced-apart sample inlets of the device; the detection region is one of a plurality of detection regions of the device; and individual detection regions of the plurality of detection regions are fluidically connected to at least one of the plurality of sample inlets.

BX: The device according to paragraph BW, further comprising at least one reservoir, wherein individual detection regions of the plurality of detection regions are fluidically connected to at least one of the at least one reservoir.

BY: A method, comprising: disposing a fluidic sample comprising a target over a reflective surface; irradiating the reflective surface using a spot of light; and detecting resultant light from the reflective surface.

BZ: The method according to paragraph BY, further comprising causing the fluidic sample to flow through a flow channel across the reflective surface and causing the spot of light to move with respect to the reflective surface at least partly across the flow channel.

CA: The method according to paragraph BY or BZ, wherein the fluidic sample comprises a liquid.

CB: The method according to any of paragraphs BY-CA, further including causing relative motion of the spot of light and at least a portion of the fluidic sample.

CC: The method according to paragraph CB, wherein the causing relative motion comprises causing the spot of light to move with respect to the reflective surface.

CD: The method according to paragraph CC, wherein the causing relative motion comprises moving the reflective surface with respect to the spot of light.

CE: The method according to any of paragraphs CB-CD, wherein the causing relative motion comprises causing the at least a portion of the fluidic sample to flow across the reflective surface substantially in a flow direction.

CF: The method according to paragraph CE, wherein the causing relative motion further comprises causing motion of the spot of light relative to the reflective surface (e.g., concurrently with the causing the at least a portion of the fluidic sample to flow across the reflective surface).

CG: The method according to paragraph CF, further comprising causing relative motion of the spot of light in a direction substantially different from (e.g., substantially perpendicular to) the flow direction.

CH: The method according to any of paragraphs BY-CG, further comprising drying the fluidic sample after the disposing and before the irradiating.

CI: The method according to any of paragraphs BY-CH, wherein the reflective surface comprises a reflective grating.

CJ: The method according to any of paragraphs BY-CI, wherein the reflective surface comprises a substantially flat surface.

CK: The method according to any of paragraphs BY-CJ, wherein the reflective surface is associated with a disc; and wherein the method further comprises: rotating the disc, wherein the disc moves with respect to the spot of light during the rotating and the reflective surface comprises at least one track; irradiating the reflective surface during the rotating; and causing the spot of light to move to follow the track of the reflective surface.

CL: The method according to paragraph CK, further comprising maintaining a focus of the spot of light with respect to the reflective surface concurrently with the rotating.

CM: The method according to any of paragraphs BY-CL, further comprising: applying a dye to the fluidic sample before the disposing; and detecting light emitted by the dye in response to the irradiating using the spot of light.

CN: The method according to any of paragraphs BY-CM, wherein the target comprises at least two portions having respective, different refractive indices.

CO: The method according to paragraph CN, wherein the fluidic sample has a refractive index different from each of the refractive indices of the target.

CP: The method according to any of paragraphs BY-CO, further comprising adjusting a focal position of the spot of light with respect to the reflective surface.

CX: The method according to any of paragraphs BY-CP, further comprising adjusting a focal position of the spot of light with respect to the reflective surface.

CY: A computer-readable medium, e.g., a computer storage medium, having thereon computer-executable instructions, the computer-executable instructions upon execution configuring a computer to perform operations as recited in any of paragraphs BY-CX.

CZ: A device comprising: a processor; and a computer-readable medium, e.g., a computer storage medium, having thereon computer-executable instructions, the computer-executable instructions upon execution by the processor configuring the device to perform operations as recited in any of paragraphs BY-CX.

DA: A system comprising: means for processing; and means for storing having thereon computer-executable instructions, the computer-executable instructions including means to configure the system to carry out a method as recited in any of paragraphs BY-CX.

DB: An assembly, comprising: a target holder configured to retain a target in a detection region; a reflective surface configured to reflect at least part of a focused spot of light to provide resultant light; an irradiation system configured to irradiate at least part of the detection region with the focused spot of light; a motion system configured to cause motion of the focused spot of light relative to the reflective surface; and a detection system configured to detect the resultant light.

DC: The assembly according to paragraph DB, further comprising at least one of the features listed in any of paragraphs AG-BI.

DD: An assembly according to any of paragraphs AF-BI, DB, or DC, wherein the target holder comprises a device as recited in any of paragraphs BJ-BX.

Conclusion

In view of the foregoing, various aspects provide effective detection or size measurement of small particles. A technical effect of various aspects is to measure physical properties of a sample, e.g., a sample of blood or another bodily fluid. Some examples use in-focus spots to provide a small spot size, which can improve detection accuracy and can permit detecting small particles. Some examples of in-focus spots permit using a phase grating to improve detection sensitivity. The claims are not limited to implementations that address any of the example use cases described herein. The claims are also not limited to implementations that address any identified deficiencies of any prior schemes.

Various examples use optical readouts to detect biological or other nanoparticles or other targets. Various examples use BLU-RAY readout optics or discs to increase resolution and detect targets much smaller than some prior schemes can detect. Various examples permit detecting small biological particles without pre-treatment that is likely to kill cells, such as drying or exposure to high vacuum. Various examples use TPP signals to detect particles, unlike optical-storage configurations that use HF signals to detect pits and lands. Various examples include LOC structures that move fluid samples via capillary action, permitting effectively measuring samples without requiring vacuum pumps. Various examples permit measuring multiple samples on a single LOC.

Although the techniques have been described in language specific to structural features and/or methodological acts, it is to be understood that the appended claims are not necessarily limited to the features and/or acts described. Rather, the features and acts are described as example implementations of such techniques. For example, network 1850, processor 1886, and other structures described herein for which multiple types of implementing devices or structures are listed can include any of the listed types, and/or multiples and/or combinations thereof.

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

The operations of the example processes are illustrated in individual blocks and summarized with reference to those blocks. The processes are illustrated as logical flows of blocks, each block of which can represent one or more operations that can be implemented in hardware, software, and/or a combination thereof. In the context of software, the operations represent computer-executable instructions stored on one or more computer-readable media that, when executed by one or more processors, enable the one or more processors to perform the recited operations. Generally, computer-executable instructions include routines, programs, objects, modules, components, data structures, and the like that perform particular functions and/or implement particular abstract data types. The order in which the operations are described is not intended to be construed as a limitation, and any number of the described operations can be executed in any order, combined in any order, subdivided into multiple sub-operations, and/or executed in parallel to implement the described processes. The described processes can be performed by resources associated with one or more data-processing systems 1801 or 1802 or other computing device(s), or components thereof, such as one or more internal and/or external CPUs and/or GPUs, and/or one or more pieces of hardware logic such as FPGAs, DSPs, and/or other types described above.

All of the methods and processes described above can be embodied in, and fully automated via, software code modules executed by one or more general purpose computers and/or processors. The code modules can be stored in any type of computer-readable storage medium and/or other computer storage device. Some and/or all of the methods can be embodied in specialized computer hardware.

Conditional language such as, among others, "can," "could," "might" and/or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples and/or that one or more examples necessarily include logic for deciding, with and/or without user input and/or prompting, whether certain features, elements and/or steps are included and/or are to be performed in any particular example. The word "or" and the phrase "and/or" are used herein in an inclusive sense unless specifically stated otherwise. Accordingly, conjunctive language such as the phrases "X, Y, or Z," "X, Y, and/or Z," or "at least one of X, Y or Z," unless specifically stated otherwise, is to be understood as signifying that an item, term, etc., can be either X, Y, or Z, or a combination thereof.

Any routine descriptions, elements and/or blocks in the flow diagrams described herein and/or depicted in the attached figures should be understood as potentially representing modules, segments, and/or portions of code that include one or more executable instructions for implementing specific logical functions and/or elements in the routine. Alternative implementations are included within the scope of the examples described herein in which elements and/or functions can be deleted and/or executed out of order from any order shown or discussed, including substantially synchronously and/or in reverse order, depending on the functionality involved as would be understood by those skilled in the art. It should be emphasized that many variations and modifications can be made to the above-described examples, the elements of which are to be understood as being among other acceptable examples. All such modifications and variations are intended to be included herein within the scope of this disclosure. Moreover, in the claims, any reference to a group of items provided by a preceding claim clause is a reference to at least some of the items in the group of items, unless specifically stated otherwise.

The invention is inclusive of combinations of the aspects described herein. References to "a particular aspect" (or "embodiment" or "version") and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting.

The invention claimed is:

1. An assembly, comprising:
   a target holder configured to retain a target in a detection region, wherein the target holder comprises a reflective surface configured to reflect at least part of a focused spot of light to provide resultant light;
   an irradiation system configured to irradiate at least part of the detection region with the focused spot of light;
   a motion system configured to cause motion of the focused spot of light relative to the reflective surface;
   a detection system configured to detect the resultant light; and
   a sample-delivery system configured to apply a fluidic sample comprising the target to the at least part of the detection region;
   wherein:
      the reflective surface comprises a reflective grating;
      the irradiation system is further configured to provide the focused spot of light comprising light of a predetermined wavelength;
      the irradiation system comprises a lens having a predetermined numerical aperture and being arranged to focus the light of the predetermined wavelength to provide the focused spot of light;

the reflective grating has a pitch exceeding a reference pitch substantially equal to a result of dividing the predetermined wavelength by twice the numerical aperture;

the fluidic sample comprises a fluid having a predetermined refractive index; and the reflective grating includes at least one groove having a depth substantially between a first reference value and a second reference value, the first reference value being the result of dividing the predetermined wavelength by the product of sixteen and the refractive index and the second reference value being substantially three times the first reference value.

2. The assembly according to claim 1, wherein:
the detection system comprises at least one split photodetector configured to provide a plurality of detection signals; and
the assembly further comprises a data-processing system configured to determine, based at least in part on at least two of the plurality of detection signals, at least one of a sum signal, a transverse push-pull signal, or a radial push-pull signal.

3. The assembly according to claim 2, wherein:
the detection system further comprises at least one optical detector configured to detect light of a different wavelength than the predetermined wavelength and to provide a detection signal corresponding to the light of the different wavelength.

4. The assembly according to claim 3, further comprising a gating system configured to provide a particle signal associated with a temporal overlap between at least one of the plurality of detection signals and the detection signal corresponding to the light of the different wavelength.

5. The assembly according to claim 1, wherein:
the motion system is further configured to cause relative motion of the focused spot of light substantially across the at least one groove.

6. A system, comprising:
a substrate;
a sample inlet associated with the substrate;
a reflective grating associated with the substrate;
an irradiation system configured to irradiate at least part of a detection region of the reflective grating with a focused spot of light that comprises light of a predetermined wavelength;
a motion system configured to cause motion of the focused spot of light relative to the reflective grating;
a detection system configured to detect resultant light reflected from the reflective grating; and
a sample-delivery system configured to apply a fluidic sample comprising a target to at least part of the detection region;
wherein:
the reflective grating is configured to retain the fluidic sample in the detection region;
the detection region is fluidically connected to the sample inlet; and
the detection region is operatively arranged with respect to the reflective grating so that at least a portion of light passing through the detection region towards the reflective grating also passes through the detection region after reflecting off the reflective grating; and
wherein:
the irradiation system comprises a lens having a predetermined numerical aperture and being arranged to focus the light of the predetermined wavelength to provide the focused spot of light;

the reflective grating has a pitch exceeding a reference pitch substantially equal to a result of dividing the predetermined wavelength by twice the numerical aperture;

the fluidic sample comprises a fluid having a predetermined refractive index; and the reflective grating includes at least one groove having a depth substantially between a first reference value and a second reference value, the first reference value being the result of dividing the predetermined wavelength by the product of sixteen and the refractive index and the second reference value being substantially three times the first reference value.

7. The system according to claim 6, further including a cover spaced apart from the reflective grating and arranged so that the detection region is at least partly between the reflective grating and the cover, wherein the cover is at least partly transparent to the at least a portion of the light of the predetermined wavelength.

8. The system according to claim 6, further comprising a reservoir fluidically connected to the detection region and spaced apart from the sample inlet.

9. The system according to claim 6, wherein the reflective grating comprises at least one groove, and the at least one groove comprises at least two of: a spiral groove portion, a straight groove portion, or a circular groove portion.

10. The system according to claim 6, wherein:
the sample inlet is configured to receive a provided sample; and
the system further comprises a filter element operatively arranged to filter the provided sample to provide the fluidic sample.

11. The system according to claim 6, wherein the substrate is a disc-format substrate.

12. The system according to claim 6, wherein:
the sample inlet is one of a plurality of spaced-apart sample inlets associated with the substrate;
the detection region is one of a plurality of detection regions associated with the substrate; and
individual detection regions of the plurality of detection regions are fluidically connected to at least one of the plurality of sample inlets.

13. A method, comprising:
disposing a fluidic sample comprising a target over a reflective surface that comprises a reflective grating;
irradiating the reflective surface using a focused spot of light that comprises light of a predetermined wavelength; and
detecting resultant light from the reflective surface;
wherein:
the method comprises focusing the light of the predetermined wavelength using a lens having a predetermined numerical aperture to provide the focused spot of light;
the reflective grating has a pitch exceeding a reference pitch substantially equal to a result of dividing the predetermined wavelength by twice the numerical aperture;
the fluidic sample comprises a fluid having a predetermined refractive index; and
the reflective grating includes at least one groove having a depth substantially between a first reference value and a second reference value, the first reference value being the result of dividing the predetermined wavelength by the product of sixteen and the refractive index and the second reference value being substantially three times the first reference value.

14. The method according to claim 13, further comprising causing the fluidic sample to flow through a flow channel across the reflective surface and causing the spot of light to move with respect to the reflective surface at least partly across the flow channel.

15. The method according to claim 13, wherein the reflective surface is associated with a disc; and
   wherein the method further comprises:
      rotating the disc, wherein the disc moves with respect to the spot of light during the rotating and the reflective surface comprises at least one track;
      irradiating the reflective surface during the rotating; and
      causing the spot of light to move to follow the track of the reflective surface.

16. The method according to claim 13, further comprising:
   applying a dye to the fluidic sample before the disposing; and
   detecting light emitted by the dye in response to the irradiating using the spot of light.

17. The method according to claim 13, wherein the target comprises at least two portions having respective, different refractive indices.

18. The method according to claim 17, wherein the predetermined refractive index is different from each of the refractive indices of the target.

* * * * *